United States Patent [19]
Detering et al.

[11] Patent Number: 5,935,293
[45] Date of Patent: *Aug. 10, 1999

[54] FAST QUENCH REACTOR METHOD

[75] Inventors: Brent A. Detering; Alan D. Donaldson; James R. Fincke; Peter C. Kong; Ray A. Berry, all of Idaho Falls, Id.

[73] Assignee: Lockheed Martin Idaho Technologies Company, Idaho Falls, Id.

[ * ] Notice: This patent is subject to a terminal disclaimer.

[21] Appl. No.: 09/076,922

[22] Filed: May 12, 1998

Related U.S. Application Data

[63] Continuation-in-part of application No. 08/404,395, Mar. 14, 1995, Pat. No. 5,749,937.

[51] Int. Cl.$^6$ .................................. C22B 4/04; C22B 4/06
[52] U.S. Cl. ......................... 75/10.19; 75/10.21; 75/399; 420/590
[58] Field of Search ................................ 75/10.19, 10.21, 75/399; 420/590

[56] References Cited

U.S. PATENT DOCUMENTS

| | | | |
|---|---|---|---|
| 4,561,883 | 12/1985 | Mullner | 75/10.19 |
| 4,801,435 | 1/1989 | Tylko | 75/10.19 |
| 5,749,937 | 5/1998 | Detering et al. | 75/10.19 |

*Primary Examiner*—Melvyn Andrews
*Attorney, Agent, or Firm*—Thorpe North & Western

[57] ABSTRACT

A fast quench reaction includes a reactor chamber having a high temperature heating means such as a plasma torch at its inlet and a means of rapidly expanding a reactant stream, such as a restrictive convergent-divergent nozzle at its outlet end. Metal halide reactants are injected into the reactor chamber. Reducing gas is added at different stages in the process to form a desired end product and prevent back reactions. The resulting heated gaseous stream is then rapidly cooled by expansion of the gaseous stream.

23 Claims, 8 Drawing Sheets

FAST QUENCH REACTOR METHOD

RELATED APPLICATION

This application is a continuation-in-part of application Ser. No. 08/404,395 filed Mar. 14, 1995 now U.S. Pat. No. 5,749,937.

CONTRACTUAL ORIGIN OF THE INVENTION

The United States Government has rights in this invention disclosed under contract number DE-AC07-76ID01570 between the U.S. Department of Energy and EG&G Idaho, Inc., now contract number DE-AC07-94ID13223 with Lockheed Idaho Technologies Company.

TECHNICAL FIELD

This disclosure pertains to equipment for thermal conversion of reactants to desired end products, which might be either a gas or ultrafine solid particles. It also relates specifically to methods for effectively producing such end products.

BACKGROUND OF THE INVENTION

The present reactor and method are intended for high temperature reactions that require rapid cooling to freeze the reaction products to prevent back reactions or decompositions to undesirable products. They use adiabatic and isentropic expansion of gases in a converging-diverging nozzle for rapid quenching. This expansion can result in cooling rates exceeding $10^{10}$ K/s, thus preserving reaction products that are in equilibrium only at high temperatures.

The concepts of this reactor were originally developed in a study of hydrogen reduction of titanium tetrachloride. When the concept was found to provide the high quench rates required to produce titanium, the concept was then applied to other processes requiring rapid quenching, including conversion of methane to acetylene.

Titanium's properties of high corrosion resistance and strength, combined with its relatively low density, result in titanium alloys being ideally suited to many high technology applications, particularly in aerospace systems. Applications of titanium in chemical and power plants are also attractive.

Unfortunately, the widespread use of titanium has been severely limited by its high cost. The magnitude of this cost is a direct consequence of the batch nature of the conventional Kroll and Hunter processes for metal production, as well as the high energy consumption rates required by their usage.

The large scale production processes used in the titanium industry have been relatively unchanged for many years. They involve the following essential steps: (1) Chlorination of impure oxide ore, (2) purification of $TiCl_4$ (3) reduction by sodium or magnesium to produce titanium sponge, (4) removal of sponge, and (5) leaching, distillation and vacuum remelting to remove Cl, Na, and Mg impurities. The combined effects of the inherent costs of such processes, the difficulty associated with forging and machining titanium and, in recent years, a shortfall in sponge availability, have contributed to relatively low titanium utilization.

One of the most promising techniques currently undergoing development to circumvent the high cost of titanium alloy parts is powder metallurgy for near net shape fabrication. For instance, it has been estimated that for every kilogram of titanium presently utilized in an aircraft, 8 kilograms of scrap are created. Powder metallurgy can substantially improve this ratio. Although this technology essentially involves the simple steps of powder production followed by compaction into a solid article, considerable development is currently underway to optimize the process such that the final product possesses at least equal properties and lower cost than wrought or cast material.

One potential powder metallurgy route to titanium alloy parts involves direct blending of elemental metal powders before compaction. Presently, titanium sponge fines from the Kroll process are used, but a major drawback is their high residual impurity content (principally chlorides), which results in porosity in the final material. The other powder metallurgy alternative involves direct use of titanium alloy powder subjected to hot isostatic pressing.

Several programs are currently involved in the optimization of such titanium alloy powders. Results are highly promising, but all involve Kroll titanium as a starting material. Use of such existing powders involves a number of expensive purification and alloying steps.

The present disclosure is the result of research to develop a new plasma process for direct and continuous production of high purity titanium powder and/or ingot. The previously-described steps (1) and (2) of the Kroll or Hunter processes are retained in this process, but steps (3), (4), and (5) are replaced by a single, high temperature process. This new process can directly produce high purity titanium from $TiCl_4$ and eliminates the need for subsequent purification steps.

Depending upon collection conditions encountered in the present process, the resulting titanium product can be either a powder suitable for the elemental blend approach to powder metallurgy or in an ingot or sponge-substitute. Titanium alloy powders and other materials can also be produced in a single step process by such direct plasma production systems.

The formation of titanium under plasma conditions has received intermittent attention in the literature over the last 30 years. Reports have generally been concerned with the hydrogen reduction of titanium tetrachloride or dioxide with some isolated references to sodium or magnesium reduction.

The use of hydrogen for reducing titanium tetrachloride has been studied in an arc furnace. Only partial reduction took place at 2100 K. The same reaction system has been more extensively studied in a plasma flame and patented for the production of titanium subchloride (German Patent 1,142,159, Jan. 10, 1963) and titanium metal (Japanese Patents 6854, May 23, 1963; 7408, Oct. 15, 1955; U.S. Pat. No. 3,123,464, Mar. 3, 1964).

Although early thermodynamic calculations indicated that the reduction of titanium tetrachloride to metallic titanium by hydrogen could start at 2500 K, the system is not a simple one. Calculations show that the formation of titanium subchloride would be thermodynamically more favorable in that temperature region.

U.S. Pat. No. 3,123,464, Mar. 3, 1964, claims that reduction of titanium tetrachloride to liquid titanium can be successfully carried out by heating the reactants ($TiCl_4$ and $H_2$) at least to, and preferably in excess of, the boiling point of titanium (3535 K). At such a high temperature, it was claimed that while titanium tetrachloride vapor is effectively reduced by atomic hydrogen, the tendency of $H_2$ to dissolve in or react with Ti is insignificant, the HCl formed is only about 10% dissociated, and the formation of titanium subchlorides could be much less favorable. The titanium vapor product is then either condensed to liquid in a water-cooled steel condenser at about 3000 K, from which it overflows into a mold, or is flash-cooled by hydrogen to powder, which is collected in a bin. Since the liquid titanium was condensed from gas with only gaseous by-products or impurities, its purity, except for hydrogen, was expected to be high.

Japanese Patent 7408, Oct. 15, 1955, described reaction conditions as follows: a mixture of $TiCl_4$ gas and $H_2$ (50% in excess) is led through a 5 mm inside diameter nozzle of a tungsten electrode at a rate of $4 \times 10^{-3} m^3/min$ and an electric discharge (3720 V and 533 mA) made to another electrode at a distance of 15 mm. The resulting powdery crystals are heated in vacuo to produce 99.4% pure titanium.

In neither of the above patents is the energy consumption clearly mentioned. Attempts to develop the hydrogen reduction process on an industrial scale were made using a skull-melting furnace, but the effort was discontinued. More recently, a claim was made that a small quantity of titanium had been produced in a hydrogen plasma, but this was later retracted when the product was truly identified as titanium carbide.

In summary, the history of attempts to treat $TiCl_4$ in hydrogen plasmas appears to indicate that only partial reduction, i.e., to a mixture of titanium and its subchlorides, is possible unless very high temperatures (>4000 K) are reached. Prior researchers have concluded that extremely rapid, preferential condensation of vapor phase titanium would be required in order to overcome the unfavorable thermodynamics of the system.

A second exemplary application of the present equipment and method pertains to production of acetylene from methane.

Natural gas (where methane is the main hydrocarbon) is a low value and underutilized energy resource in the U.S. Huge reserves of natural gas are known to exist in remote areas of the continental U.S., but this energy resource cannot be transported economically and safely from those regions. Conversion of natural gas to higher value hydrocarbons has been researched for decades with limited success in today's economy.

Recently, there have been efforts to evaluate technologies for the conversion of natural gas (which is being flared) to acetylene as a feed stock for commodity chemicals. The ready availability of large natural gas reserves associated with oil fields and cheap labor might make the natural gas to acetylene route for producing commodity chemicals particularly attractive in this part of the world.

Acetylene can be used as a feed stock for plastic manufacture or for conversion by demonstrated catalyzed reactions to liquid hydrocarbon fuels. The versatility of $C_2H_2$ as a starting raw material is well known and recognized. Current feed stocks for plastics are derived from petrochemical based raw materials. Supplies from domestic and foreign oil reserves to produce these petrochemical based raw materials are declining, which puts pressure on the search for alternatives to the petrochemical based feed stock. Therefore, the interest in acetylene based feed stock has currently been rejuvenated.

Thermal conversion of methane to liquid hydrocarbons involves indirect or direct processes. The conventional methanol-to-gasoline (MTG) and the Fischer-Tropsch (FT) processes are two prime examples of such indirect conversion processes which involve reforming methane to synthesis gas before converting to the final products. These costly endothermic processes are operated at high temperatures and high pressures.

The search for direct catalytic conversion of methane to light olefins (e.g. $C_2H_4$) and then to liquid hydrocarbons has become a recent focal point of natural gas conversion technology. Oxidative coupling, oxyhydrochlorination, and partial oxidation are examples of direct conversion methods. These technologies require operation under elevated pressures, moderate temperatures, and the use of catalysts. Development of special catalysts for direct natural gas conversion process is the biggest challenge for the advancement of these technologies. The conversion yields of such processes are low, implementing them is costly in comparison to indirect processes, and the technologies have not been proven.

Light olefins can be formed by very high temperature (>1800° C.) abstraction of hydrogen from methane, followed by coupling of hydrocarbon radicals. High temperature conversion of methane to acetylene by the reaction $2CH_4 \rightarrow C_2H_2 + 3H_2$ is an example. Such processes have existed for a long time.

Methane to acetylene conversion processes currently use cold liquid hydrocarbon quenchants to prevent back reactions. Perhaps the best known of these is the Huels process which as been in commercial use in Germany for many years. The electric arc reactor of Huels transfers electrical energy by 'direct' contact between the high-temperature arc (15000–20000 K) and the methane feed stock. The product gas is quenched with water and liquefied propane to prevent back reactions. Single pass yields of acetylene are less than 40% for the Huels process. Overall $C_2H_2$ yields are increased to 58% by recycling all of the hydrocarbons except acetylene and ethylene.

Although in commercial use, the Huels process is only marginally economical because of the relatively low single pass efficiencies and the need to separate product gases from quench gases. Subsidies by the German Government have helped to keep this process in production.

Westinghouse has employed a hydrogen plasma reactor for the cracking of natural gas to produce acetylene. In the plasma reactor, hydrogen is fed into the arc zone and heated to a plasma state. The exiting stream of hot $H_2$ plasma at temperatures above 5000 K is mixed rapidly with the natural gas below the arc zone, and the electrical energy is indirectly transferred to the feed stock. The hot product gas is quenched with liquefied propane and water, as in the Huel process, to prevent back reactions. However, as with the Huels process, separation of the product gas from quench gas is needed. Recycling all of the hydrocarbons except acetylene and ethylene has reportedly increased the overall yield to 67%. The $H_2$ plasma process for natural gas conversion has been extensively tested on a bench scale, but further development and demonstration on a pilot scale is required.

The Scientific and Industrial Research Foundation (SINTEF) of Norway has developed a reactor consisting of concentric, resistance-heated graphite tubes. Reaction cracking of the methane occurs in the narrow annular space between the tubes where the temperature is 1900 to 2100 K. In operation, carbon formation in the annulus led to significant operational problems. Again, liquefied quenchant is used to quench the reaction products and prevent back reactions. As with the previous two acetylene production processes described above, separation of the product gas from quench gas is needed. The overall multiplepass acetylene yield from the resistance-heated reactor is about 80% and the process has been tested to pilot plant levels.

Like the Huels reactor, the present fast quench reactor can use an electric arc plasma process to crack the methane, but it requires no quenchant to prevent back reactions. In this manner it eliminates any need for extensive separation.

SUMMARY OF THE INVENTION

This invention relates to a reactor and method for producing desired end products by injecting reactants into the inlet end of a reactor chamber; rapidly heating the reactants to produce a hot reactant stream which flows toward the outlet end of the reactant chamber, the reactor chamber having a predetermined length sufficient to effect heating of the reactant stream to a selected equilibrium temperature at which the desired end product is available within the reactant stream as a thermodynamically stable reaction product at a location adjacent to the outlet end of the reaction chamber; passing the gaseous stream through a restrictive convergent-divergent nozzle arranged coaxially within the remaining end of the reactor chamber to rapidly cool the gaseous stream by converting thermal energy to kinetic energy as a result of adiabatic and isentropic expansion as it flows axially through the nozzle and minimizing back reactions, thereby retaining the desired end product within the flowing gaseous stream; and subsequently cooling and slowing the velocity of the desired end product and remaining gaseous stream exiting from the nozzle. Preferably the rapid heating step is accomplished by introducing a stream of plasma arc gas to a plasma torch at the inlet end of the reactor chamber to produce a plasma within the reactor chamber which extends toward its outlet end.

An alternate method of this invention uses a virtual convergent-divergent nozzle. This is accomplished by directing one or more streams of particles, droplets, liquid, or gas into the main flow stream of the reaction chamber such that the main reactant flow stream is forced to flow as though a real convergent-divergent nozzle were present. This phenomena occurs because the reduced axial momentum of the directing flow effectively impedes the flow of the main stream, thereby forcing the majority of the main stream to flow around the impeding stream, similar to the flow through the restriction of a conventional converging-diverging nozzle. A similar cooling effect is achieved with the virtual nozzle. The directing or impeding stream(s) can play other roles than merely providing the virtual nozzle effect. In addition to keeping the main flow stream away from the wall, they can interact with the main stream further downstream in various ways to provide, for example, enhanced heat transfer, mixing, chemical reaction, etc. The virtual nozzle effect can also be utilized in combination with a conventional converging-diverging nozzle to achieve optimal performance. To obtain the desired expansion and cooling it will be necessary to adjust the velocity of the reactants, the quantity of the reactants, the number and position of the supply inlets, and diameter of the reaction chamber.

In the production of metals by means of metal halides and a reducing gas it has also been found of special value to add the reducing gas in at least two different positions in the reaction chamber. The first injection will occur prior to or at the time the metal halide reaches the desired reaction temperature. Preferably this injection of reducing gas will be prior to or at the time of the injection of the metal halide. When hydrogen is added as the reducing gas in this manner hydrogen ion is produced which reacts with the halide ion.

A second introduction of reducing gas into the reaction chamber occurs after the first such introduction. This is preferably immediately prior to the neck of the convergent-divergent nozzle, at the neck, or immediately after the neck. This produces hydrogen molecule which acts to prevent the metal produced from reacting with any halide ion present. This same second introduction of reducing gas into the reaction chamber applies to the virtual nozzle described above. For the virtual nozzle the second introduction of reducing gas occurs after the first reducing gas is injected and preferably immediately after the reactant gas stream begins to expand.

BRIEF DESCRIPTION OF THE DRAWINGS

Preferred embodiments of the invention are described below with reference to the following drawings.

DETAILED DESCRIPTION OF THE PREFERRED EMBODIMENTS

The fast quench reactor and method of operation described in this disclosure take advantage of the high temperatures (5,000 to 20,000° C.) available in a high temperature heating means such as a thermal plasma to produce materials that are thermodynamically stable at these high temperatures. These materials include metals, alloys, intermetallics, composites, gases and ceramics.

A converging-diverging (De Laval) nozzle located downstream from the plasma and reactant addition inlet(s) produces a rapid drop in kinetic temperature in a flowing gas stream. This effectively "freezes" or stops all chemical reactions. It permits efficient collection of desired end products as the gases are rapidly cooled without achieving an equilibrium condition. Resulting end products which have been produced in the plasma at high temperature but are thermodynamically unstable or unavailable at lower temperatures can then be collected due to resulting phase changes (gas to solid) or stabilization by cooling to a lower equilibrium state (gas to gas).

The fast quench reactor and method of this invention shall be described and illustrated forthwith in terms of a rapid heating means comprising a plasma torch and a stream of plasma arc gas. However, it will be recognized that the rapid heating means can also include other rapid heating means such as lasers, and flames produced by oxidation of a suitable fuel, e.g. an oxygen/hydrogen flame.

Figure 1:
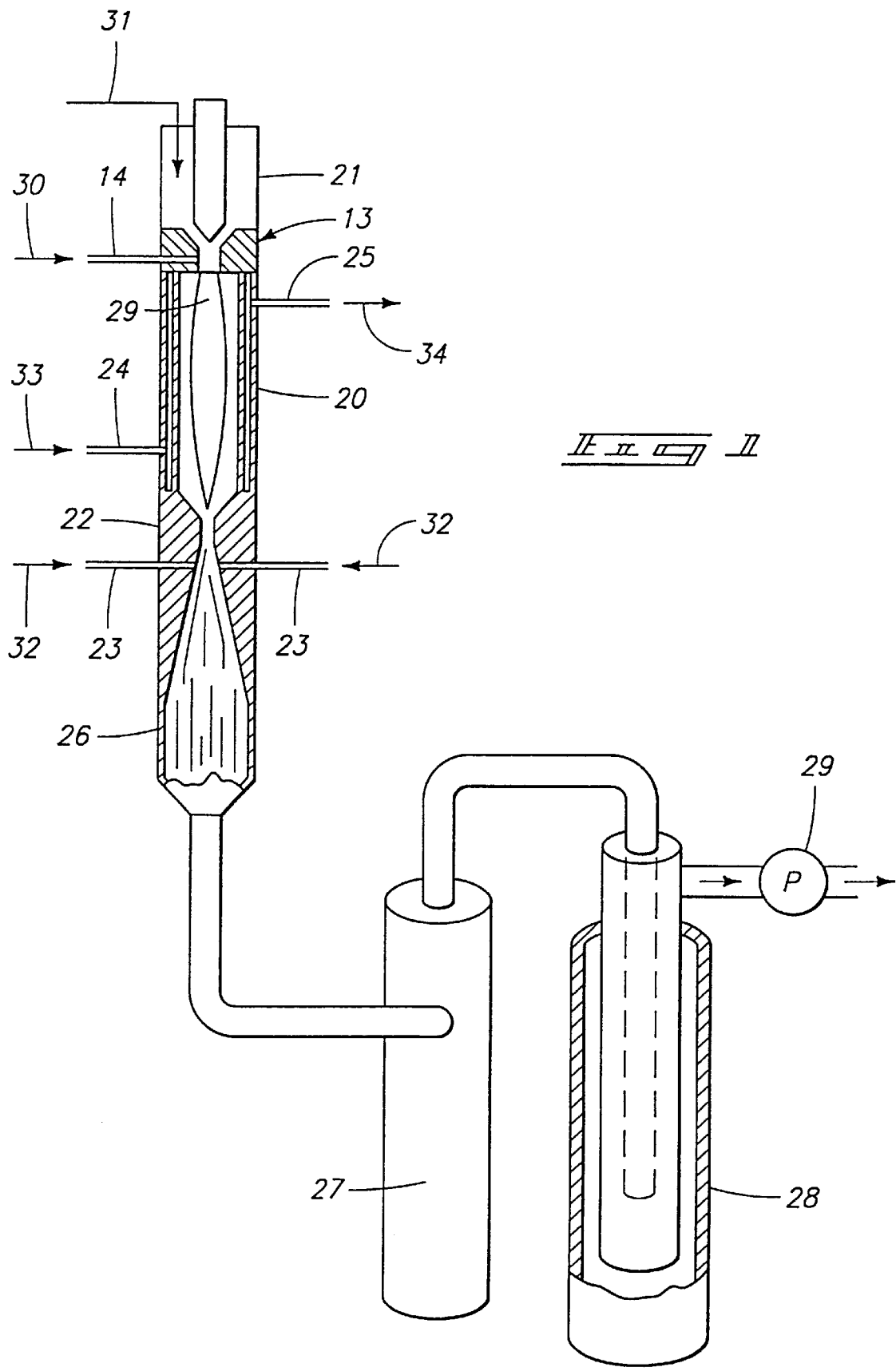
FIG. 1 is a schematic cross-sectional view of a reactor system.

A schematic diagram of an ultra fast quenching apparatus is shown in FIG. 1. An enclosed axial reactor chamber 20 includes an inlet at one end (shown to the left) and an outlet at its remaining end (shown to the right).

A plasma torch 21 is positioned adjacent to the reactor chamber. Torch 21 is used to thermally decompose an incoming gaseous stream within a resulting plasma 29 as the gaseous stream is delivered through the inlet of the reactor chamber 20.

A plasma is a high temperature luminous gas which is at least partially (1 to 100%) ionized. A plasma is made up of gas atoms, gas ions, and electrons. In the bulk phase a plasma is electrically neutral. A thermal plasma can be created by passing a gas through an electric arc. The electric arc will rapidly heat the gas by resistive and radiative heating to very high temperatures within microseconds of passing through the arc. The plasma is typically luminous at temperatures above 9000 K.

A plasma can be produced with any gas in this manner. This gives excellent control over chemical reactions in the plasma as the gas might be neutral (argon, helium, neon), reductive (hydrogen, methane, ammonia, carbon monoxide) or oxidative (oxygen, nitrogen, carbon dioxide). Oxygen or oxygen/argon gas mixtures are used to produce metal oxide ceramics and composites. Other nitride, boride, and carbide ceramic materials require gases such as nitrogen ammonia, hydrogen, methane, or carbon monoxide to achieve the correct chemical environment for synthesis of these materials.

The details of plasma generating torches are well known and need not be further detailed within this disclosure to make the present invention understandable to those skilled in this field.

An incoming stream of plasma gas is denoted by arrow 31. The plasma gas can also be a reactant or can be inert. A gaseous stream of one or more reactants (arrow 30) is normally injected separately into the plasma 29, which is directed toward the downstream outlet of the reactor chamber 20. The gaseous stream moving axially through the reactor chamber 20 includes the reactants injected into the plasma arc or within a carrier gas.

Reactant materials are usually injected downstream of the location where the arc attaches to the annular anode of the plasma generator or torch. Materials which can be injected into the arc region include natural gas, such as is used in the Huels process for the production of ethylene and acetylene from natural gas.

Gases and liquids are the preferred forms of injected reactants. Solids may be injected, but usually vaporize too slowly for chemical reactions to occur in the rapidly flowing plasma gas before the gas cools. If solids are used as reactants, they will usually be heated to a gaseous or liquid state before injection into the plasma.

A convergent-divergent nozzle 22 is coaxially positioned within the outlet of the reactor chamber 20. The converging or upstream section of the nozzle restricts gas passage and controls the residence time of the hot gaseous stream within the reactor chamber 20, allowing its contents to reach thermodynamic equilibrium. The contraction that occurs in the cross sectional size of the gaseous stream as it passes through the converging portions of nozzle 22 change the motion of the gas molecules from random directions, including rotational and vibrational motions, to straight line motion parallel to the reactor chamber axis. The dimensions of the reactor chamber 20 and the incoming gaseous flow rates are selected to achieve sonic velocity within the restricted nozzle throat.

As the confined stream of gas enters the diverging or downstream portions of the nozzle 22, it is subjected to an ultra fast decrease in pressure as a result of a gradual increase in volume along the conical walls of the nozzle exit. The resulting pressure change instantaneously lowers the temperature of the gaseous stream to a new equilibrium condition.

An additional reactant, such as hydrogen at ambient temperatures, can be tangentially injected into the diverging section of nozzle 22 (arrow 32) to complete the reactions or prevent back reactions as the gases are cooled. Supply inlets for the additional reactant gas are shown in FIG. 1 at 23.

Numerals 24 and 25 designate a coolant inlet and outlet for the double-walled structure of the reactor chamber 20. Coolant flow is indicated by arrows 33 and 34. The walls of nozzle 22 and a coaxial cool down chamber 26 downstream from it should also be physically cooled to minimize reactions along their inner wall surfaces.

Reaction particles are collectable within a cyclone separator shown generally at 27. A downstream liquid trap 28, such as a liquid nitrogen trap, can be used to condense and collect reactor products such as hydrogen chloride and ultra-fine powders within the gaseous stream prior to the gaseous stream entering a vacuum pump 29.

Figure 2:
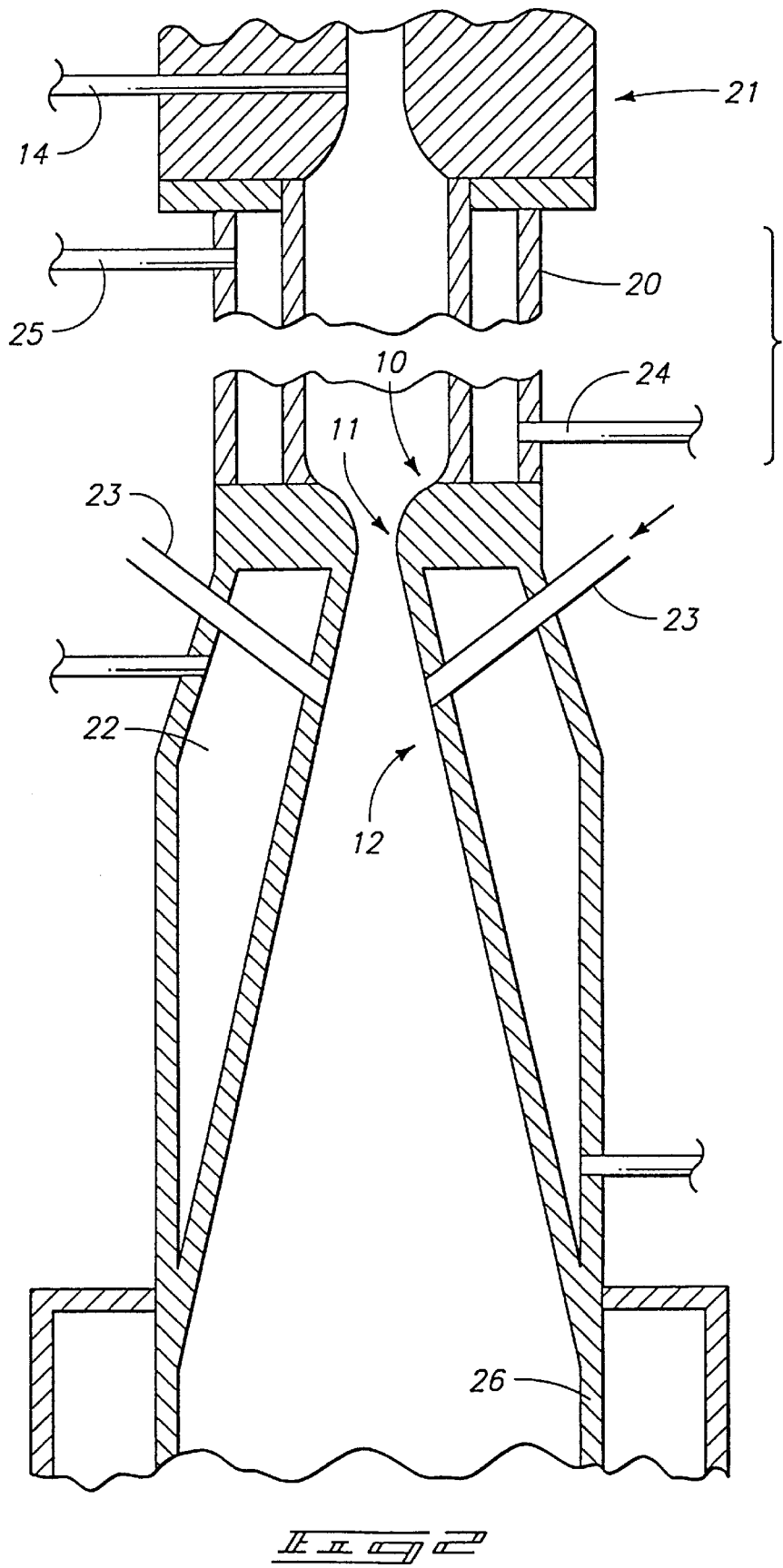
FIG. 2 is an enlarged cross-sectional view of the reactor chamber and converging-diverging nozzle.

FIG. 2 further illustrates details of the converging-diverging nozzle structure. The same reference numerals are used in FIG. 2 as in FIG. 1. By proper selection of nozzle dimensions, the reactor chamber 20 can be operated at atmospheric pressure or in a pressurized condition, while the chamber 26 downstream from nozzle 22 is maintained at a vacuum pressure by operation of pump 29. The sudden pressure change that occurs as the gaseous stream traverses nozzle 22 brings the gaseous stream to a lower equilibrium condition instantly and prevents unwanted back reactions that would occur under more drawn out cooling conditions.

Typical residence times for materials within the free flowing plasma are on the order of milliseconds. To maximize mixing with the plasma gas the reactants (liquid or gas) are injected under pressure (10 to 100 atmospheres) through a small orifice to achieve sufficient velocity to penetrate and mix with the plasma. It is preferable to use gaseous or vaporized reactants whenever practical, since this eliminates need for a phase change within the plasma and improves the kinetics of the reactor. In addition, the injected stream of reactants is injected normal (90° angle) to the flow of the plasma gases. In some cases positive or negative deviations from this 90° angle by as much as 30° may be optimum.

The high temperature of the plasma rapidly vaporizes the injected liquid materials and breaks apart gaseous molecular species to their atomic constituents. A variety of metals (titanium, vanadium, antimony, silicon, aluminum, uranium, tungsten), metal alloys (titanium/vanadium, titanium/aluminum, titanium/aluminum/vanadium), intermetallics (nickel aluminide, titanium aluminide), and ceramics (metal oxides, nitrides, borides, and carbides) can be synthesized by injecting metal halides (chlorides, bromides, iodides, and fluorides) in liquid or gaseous form into a plasma of the appropriate gas downstream from the anode arc attachment point and within the torch exit or along the length of the reactor chamber. Titanium dioxide and antimony oxide are especially preferred ultrafine powders produced according to this invention. Solid metal halide materials are preferably vaporized and injected into the plasma as a liquid or gas to improve reaction kinetics.

The reaction chamber 20 is the location in which the preferred chemical reactions occur. It begins downstream from the plasma arc inlet and terminates at the nozzle throat. It includes the reactor areas in which reactant injection/mixing and product formation occurs, as well as the converging section of the quench nozzle.

Temperature requirements within the reactor chamber and its dimensional geometry are specific to the temperature required to achieve an equilibrium state with an enriched quantity of each desired end product.

There is a substantial difference in temperature gradients and gaseous flow patterns along the length of the reaction chamber 20. At the plasma arc inlet, flow is turbulent and there is a high temperature gradient; from temperatures of about 20,000 K at the axis of the chamber to about 375 K at the chamber walls. At the nozzle throat, the gaseous flow is laminar and there is a very low temperature gradient across its restricted open area.

Since the reaction chamber is an area of intense heat and chemical activity it is necessary to construct the reactor chamber of materials that are compatible with the temperature and chemical activity to minimize chemical corrosion from the reactants, and to minimize melting degradation and ablation from the resulting intense plasma radiation. The reactor chamber is usually constructed of water cooled stainless steel, nickel, titanium, or other suitable materials. The reactor chamber can also be constructed of ceramic materials to withstand the vigorous chemical and thermal environment.

The reaction chamber walls are internally heated by a combination of radiation, convection and conduction. Cooling of the reaction chamber walls prevents unwanted melting and/or corrosion at their surfaces. The system used to control such cooling should maintain the walls at as high a temperature as can be permitted by the selected wall material, which must be inert to the reactants within the reactor chamber at the expected wall temperatures. This is true also with regard to the nozzle walls, which are subjected to heat only by convection and conduction.

The dimensions of the reactor chamber are chosen to minimize recirculation of the plasma and reactant gases and to maintain sufficient heat (enthalpy) going into the nozzle throat to prevent degradation (undesirable back or side reaction chemistry).

The length of the reactor chamber must be determined experimentally by first using an elongated tube within which the user can locate the target reaction threshold temperature. The reactor chamber can then be designed long enough so that reactants have sufficient residence time at the high reaction temperature to reach an equilibrium state and complete the formation of the desired end products. Such reaction temperatures can range from a minimum of about 1700° C. to about 4000° C.

The inside diameter of the reactor chamber 20 is determined by the fluid properties of the plasma and moving gaseous stream It must be sufficiently great to permit necessary gaseous flow, but not so large that undesirable recirculating eddys or stagnant zones are formed along the walls of the chamber. Such detrimental flow patterns will cool the gases prematurely and precipitate unwanted products, such as subchlorides or carbon. As a general rule, the inside diameter of the reactor chamber 20 should be in the range of 100 to 150% of the plasma diameter at the inlet end of the reactor chamber.

The purpose of the converging section of the nozzle is to compress the hot gases rapidly into a restrictive nozzle throat with a minimum of heat loss to the walls while maintaining laminar flow and a minimum of turbulence. This requires a high aspect ratio change in diameter that maintains smooth transitions to a first steep angle (>45°) and then to lesser angles (<45°) leading into the nozzle throat.

The purpose of the nozzle throat is to compress the gases and achieve sonic velocities in the flowing hot gaseous stream. This converts the random energy content of the hot gases to translational energy (velocity) in the axial direction of gas flow. This effectively lowers the kinetic temperature of the gases and almost instantaneously limits further chemical reactions. The velocities achieved in the nozzle throat and in the downstream diverging section of the nozzle are controlled by the pressure differential between the reactor chamber and the section downstream of the diverging section of the nozzle. Negative pressure can be applied downstream or positive pressure applied upstream for this purpose.

The purpose of the diverging section of the nozzle is to smoothly accelerate and expand gases exiting the nozzle from sonic to supersonic velocities, which further lowers the kinetic temperature of the gases.

The term "smooth acceleration" in practice requires use of a small diverging angle of less than 35 degrees to expand the gases without suffering deleterious effects of separation from the converging wall and inducing turbulence. Separation of the expanding gases from the diverging wall causes recirculation of some portion of the gases between the wall and the gas jet exiting the nozzle throat. This recirculation in turn results in local reheating of the expanding gases and undesirable degradation reactions, producing lower yields of desired end products.

Physics of the Nozzle

The super fast quench phenomena observed in this reactor is achieved by rapidly converting thermal energy in the gases to kinetic energy via a modified adiabatic and isentropic expansion through a converging-diverging nozzle. In the process, the gas temperature and pressure drop extremely fast and the gas reaches supersonic velocity. It is important to first raise the temperature of the reactants in the reactor chamber to a level at which the desired end product is more stable than other reaction products in equilibrium with it. This is normally a consequence of the fact that the free energy of the desired end product will decrease at the selected elevated temperatures in comparison to the remaining reaction products. However, this window of opportunity is very short-lived ($<10^{-3}$ sec) in a high temperature reactor. To stabilize maximum conversion of the reaction product, it is necessary to rapidly cool the emerging gas below a selected cooling temperature to force it to a lower equilibrium state and thereby prevent decomposition of the end product.

To understand the quench phenomenon in this reactor, it is necessary to investigate the changes in the temperature, pressure, and velocity of the gases as a function of changes in reactor geometry.

The reactor nozzle 22 (FIG. 2) can be divided into three sections; the convergent reaction chamber 10, the nozzle throat 11, and the divergent quench chamber 12. The entrance angle to the throat area, the cross-sectional area of the throat, and the diverging angle after the throat all exert influence on the temperature, pressure, and velocity profiles of the plasma gas.

In the converging-diverging nozzle, the gas is flowing from a higher pressure $P_0$ to a lower pressure $P_1$. During passage of the gas through the nozzle, there will be a rapid transformation of thermal energy to kinetic energy. This kinetic energy will give rise to a high gas velocity after discharging from the nozzle. The gas enters the converging section at a low velocity and will emerge at the diverging section with a higher velocity.

The velocity of the gas in the throat of the nozzle, assuming adiabatic expansion, will achieve sonic values. When the gas accelerates through the nozzle throat, the temperature of the gas will, simultaneously drop rapidly. As a result of high velocity cooling, the initial gas temperature ($T_0$) will drop to a lower temperature, $T_1$, upon exiting from the nozzle. This rapid temperature quenching through a nozzle freezes the high temperature equilibrium products of a high temperature gas phase reaction. The pressure and temperature drop resulting from adiabatic expansion in a converging-diverging nozzle is described in the following equation:

$$\left(\frac{P_0}{P_1}\right)^{\frac{\gamma-1}{\gamma}} = \frac{T_0}{T_1}$$

$P_0$, $P_1$, $T_0$ are initial and final pressures and temperatures of the gas, respectively. $\gamma$ is the ratio of $C_p/C_v$ where $C_p$ and $C_v$ are the heat capacities at constant pressure and volume, respectively. At 2500 K, $\gamma$ is 1.66 for Ar, 1.30 for $H_2$, and 1.11 for $C_2H_2$. This equation can be used to estimate the temperature drop across the nozzle throat if the initial and final pressures of the gases are known or vice versa. The mass flow rate, m, is related to the cross-sectional area (A*) of the nozzle throat, the velocity (V) and the specific volume ($\Omega$) of the gas at the throat. The specific volume ($\Omega$) is the inverse of gas density at the cross section.

$$\dot{m} = \left(\frac{V}{\Omega}\right) \times A^*$$

After substituting $T_0$, $P_0$, $\gamma$, M (molecular weight), and R (the gas constant) for V/$\Omega$, the equation takes the form:

$$\dot{m} = \left(\frac{P_0 M}{RT_0}\right)\left(\frac{\gamma RT_0}{M}\right)^{1/2} \times \left(\frac{2}{\gamma+1}\right)^{\frac{(\gamma+1)}{2(\gamma-1)}} \times A^*$$

This equation has been used to guide the design of the nozzle diameters used in the reactors built to date. Despite the assumption for constant $\gamma$ (which is valid for an argon plasma), the equation has been quite accurate in predictions of mass flow as a function of temperature, pressure, molecular weight, and nozzle diameter compared to experimental results.

The velocity of the expanding gas in mach number (Ma) is related to temperature (T), pressure (P), density ($\rho=\Omega^{-1}$), and nozzle area (A) by the following equations:

$$\frac{T_0}{T} = 1 + \frac{\gamma-1}{2}(Ma)^2$$

$$\frac{P_0}{P} = \left[1 + \frac{\gamma-1}{2}(Ma)^2\right]^{\gamma/(\gamma-1)}$$

$$\frac{\rho_0}{\rho} = \left[1 + \frac{\gamma-1}{2}(Ma)^2\right]^{\gamma/(\gamma-1)}$$

$$\frac{A}{A^*} = \frac{1}{Ma}\left\{\frac{2}{\gamma+1}\left[1 + \frac{\gamma-1}{2}(Ma)^2\right]\right\}^{(\gamma+1)/[2(\gamma-1)]}$$

In the last equation above, A* is the cross-sectional area at the throat of the nozzle, and A is the cross-sectional area of the converging-diverging section. Substituting $T_0/T$ into the equation, it becomes $$\frac{A}{A^*} = \frac{1}{Ma}\left\{\frac{2}{\gamma+1} \times \frac{T_0}{T}\right\}^{(\gamma+1)/[2(\gamma-1)]}$$

Figure 3:
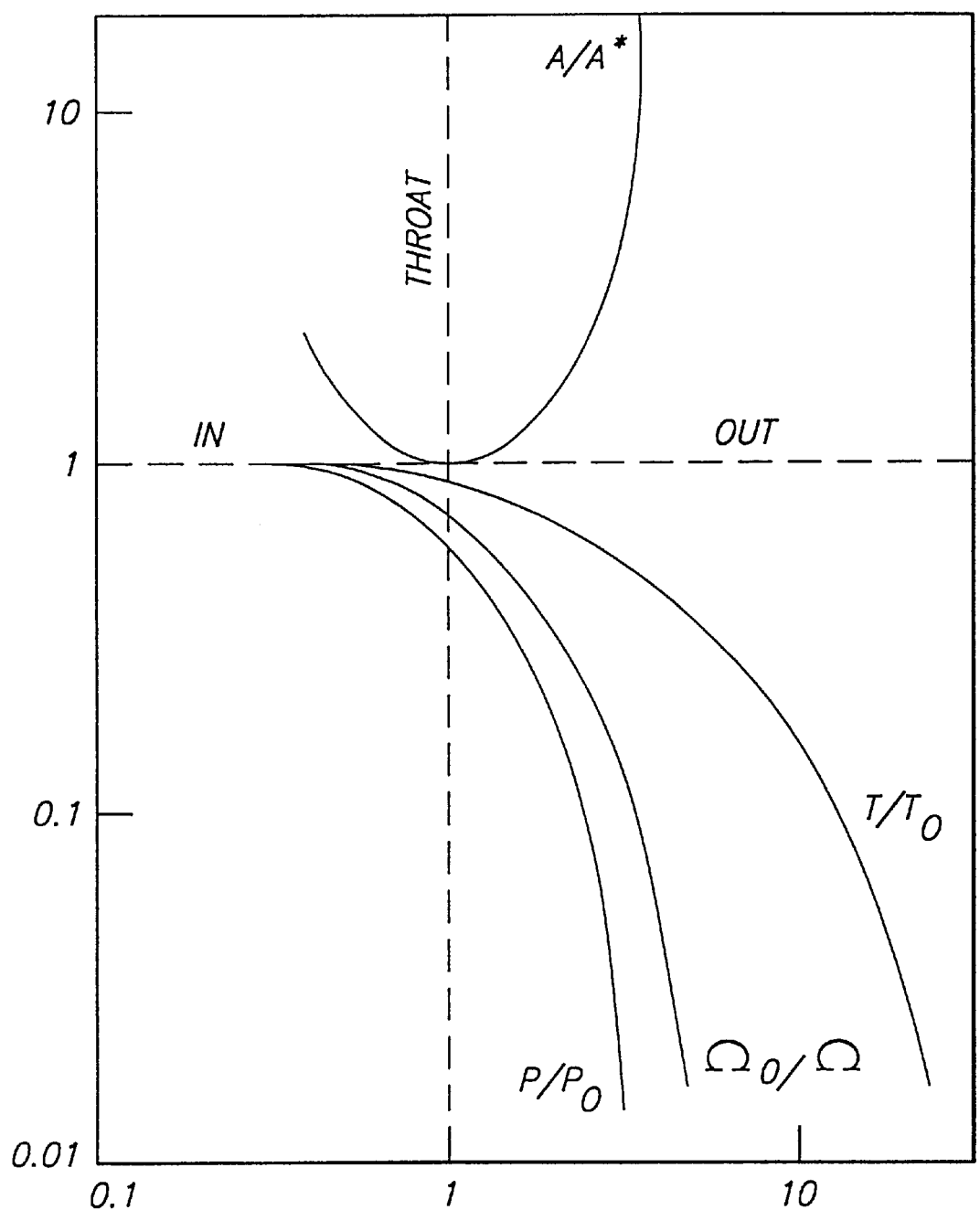
FIG. 3 is a plot of temperatures, pressures, specific volumes and nozzle throat areas as a function of gas velocity in the reactor apparatus.

FIG. 3 is a plot of $T/T_0$, $P/P_0$, $\Omega_0/\Omega$, and A/A* through a nozzle throat as a function of the gas velocity (in Ma) for $\gamma$=1.3 ($H_2$). It clearly demonstrates that both gas temperature and pressure quench rapidly upon exiting from the nozzle. The resulting high gas velocity lends itself to the application of a gas-turbine to recuperate the energy as electricity to supplement the process.

In a test case (using a 95% Ar and 5% $H_2$ plasma) if A/A*=4, Ma=2, and $\gamma$=1.66 the final temperature drops almost by a factor of 4. This type of temperature drop is easily attainable through the quench nozzle. If the final temperature in the quench chamber for a reaction is 500 K, then the initial temperature before the quench nozzle would be around 2000 K.

EXAMPLE 1

Titanium

The preferred method for producing titanium from titanium tetrachloride ($TiCl_4$) involves directing titanium tetrachloride vapor and a hydrogen into a hot plasma torch operated at 12 kW with a mixture of argon and hydrogen as the plasma gas (95% Argon: 5% Hydrogen, by volume) to decompose it to titanium and chlorine, followed by rapid expansion of the resulting hot gases and cooling with additional hydrogen to retain the titanium in an elemental solid metal state.

The diameter and length (6.0 mm×700.0 mm) of the reaction chamber was chosen to obtain maximum mixing while maintaining a minimum of 4000 K temperature at the entrance of the nozzle throat. The reaction chamber, converging/diverging nozzle were constructed from nickel 200 alloy to reduce corrosion. Standard equations were used to calculate the dimensions of the bell-shaped converging nozzle, nozzle throat diameter diverging angle, and diverging nozzle exit diameter.

Reactants: Titanium tetrachloride liquid and hydrogen gas
Plasma Torch: 10 kW laboratory plasma torch
  30 Volts, 400 Amps
  Cathode: thoriated tungsten in water cooled copper
  Anode: Water-Cooled Copper Cylinder 6.0 mm diameter× 20.0 mm in length
Plasma Gas: 95% Argon, 5% Hydrogen, Average total gas flow was maintained at 23.6 liters/min.
Reactant Injection: Gaseous (200° C.) Titanium tetrachloride at the point where the plasma plume exits the plasma torch. The hot titanium tetrachloride injection tubes, reaction chamber and converging/diverging nozzle section were constructed from nickel 200 alloy to minimize corrosion.
Injection Rate: Vaporized Titanium tetrachloride was injected at the rate of 10.0 to 15.0 milliliters/hour. This resulted in a titanium metal powder production rate of 5 grams per hour.
Reaction Chamber: Water-cooled Nickel 200 cylinder 6.0 mm×20.0 mm
Converging Nozzle: Bell shaped with 2.0 mm radii
Nozzle throat: 2.0 mm×1.0 mm in length, determined from standard equations,
Diverging Nozzle: Conical shaped with 14° included angle expanding out to a 12.0 mm diameter.
Cool down section: Water-cooled stainless steel, 12.0 mm diameter×600.0 mm
Cyclone collectors: Water-cooled stainless steel, 12.0 mm inlet and outlet diameter, 50.0 mm inside diameter body, designed to maintain high entrance and exit velocity
Off-Gas Cleanup: After product collection the process gas was passed through a liquid nitrogen cold trap and HEPA filter to remove HCl gas and residual titanium particles before the gas enter the mechanical vacuum pump.

Vacuum System: A mechanical vacuum pump was used to maintain pressure downstream from the nozzle throat at 5.0 to 10.0 Torr (mm Hg)

FIGS. 1 and 2 of the drawings pertain to an apparatus tested for recovering elemental metals from metal-containing compounds. In the described preferred embodiment, the elemental metal is titanium and the metal-containing compound is titanium tetrachloride ($TiCl_4$). However, the illustrated apparatus is suitable for use with other metals and compounds where plasma processing of the compound requires ultra fast quenching to prevent back reactions.

The plasma torch 21 located at the reactor chamber inlet thermally decomposes an incoming gaseous stream comprised of a metal-containing compound plus one or more reactants as the resulting gaseous stream moves axially through the reactor chamber 20 in conjunction with a carrier gas. The resulting hot gaseous stream is then directed through the coaxial convergent-divergent nozzle 22. The convergent portion 10 of the nozzle 22 controls the residence time of the hot gaseous stream within the reactor chamber 20, thereby allowing its contents to reach thermodynamic equilibrium. It also streamlines the flow of hot gases, converting their motion from random movement to straight line movement along the central nozzle axis. The divergent portion 12 of the nozzle 22 subjects the stream to an ultra fast decrease in pressure. Quenching streams of gas, normally at ambient temperature, are introduced into the hot gaseous stream through inlets 23 as it passes through the nozzle. This rapidly cools the contents of the hot gaseous stream at a rate that condenses the elemental metal and inhibits formation of equilibrium products.

The plasma reduction is based on a quasi equilibrium-temperature quench sequence in which the initiation of nucleation is controlled by passage of a heated gaseous stream through a converging-diverging nozzle geometry. Results from present system tests have shown the feasibility of the process. The powder product is extremely fine (~20 nm).

Figure 4:
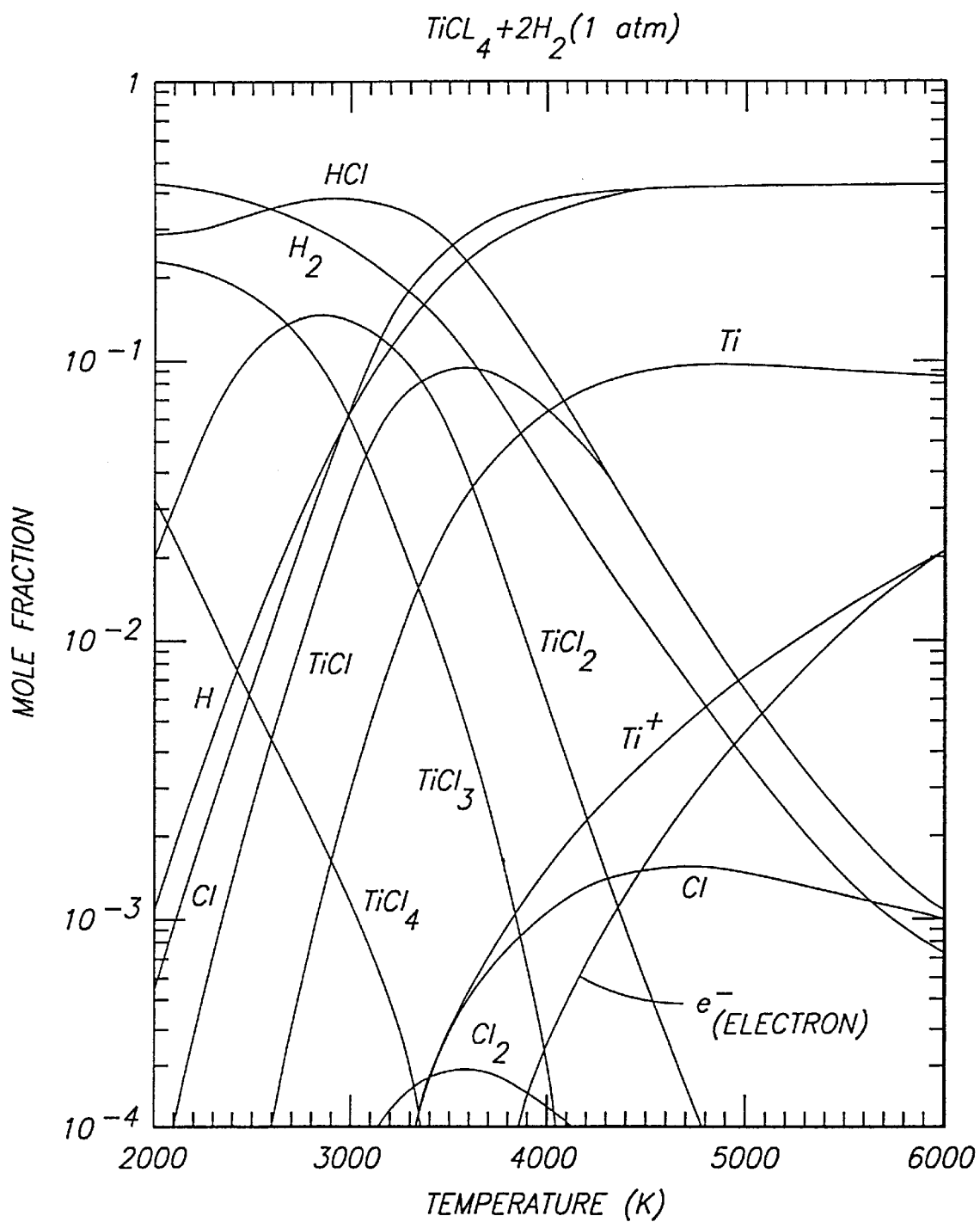
FIG. 4 is a graph plotting equilibrium concentrations in a titanium tetrachloride and hydrogen system as a function of temperature.
Figure 5:
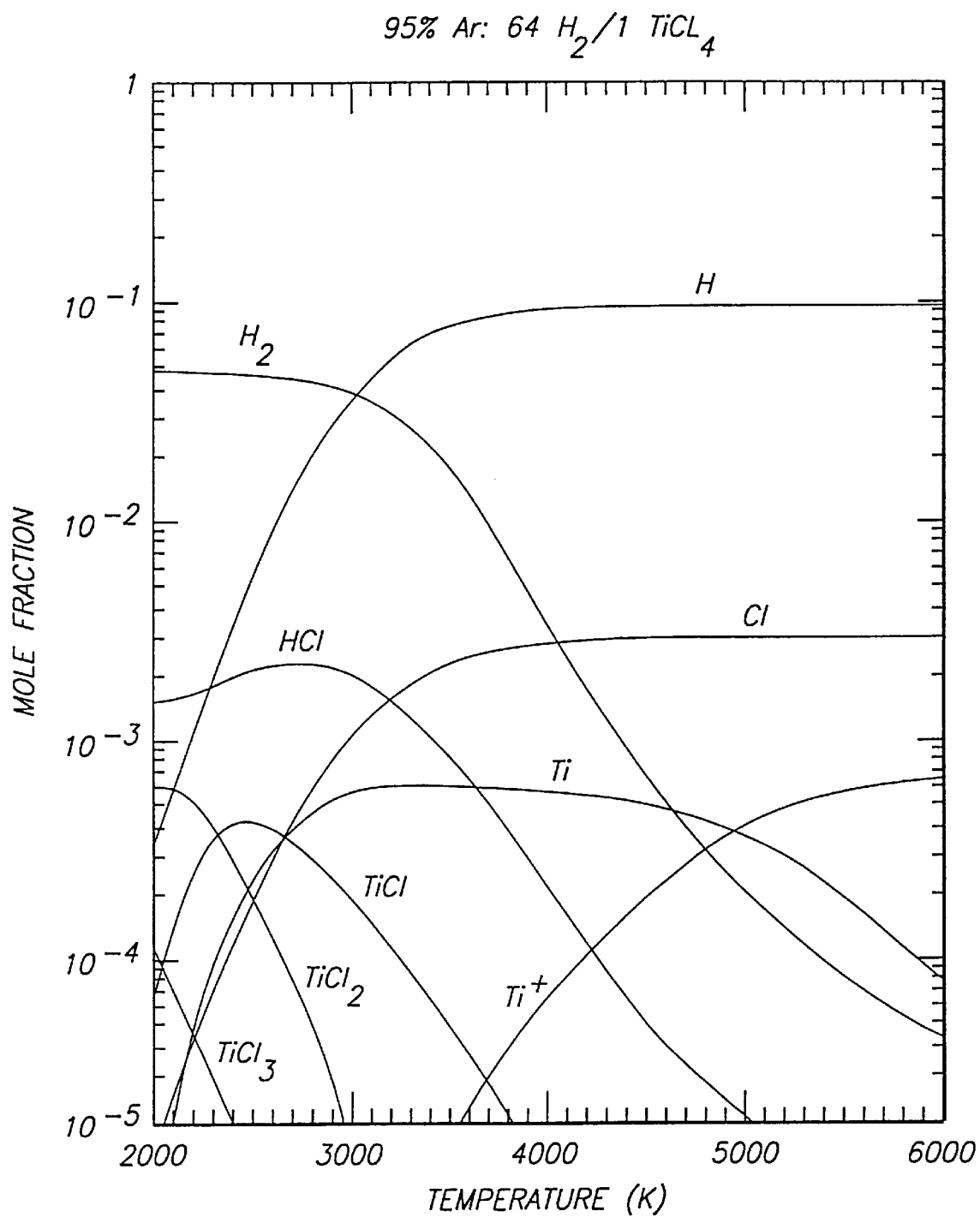
FIG. 5 is a graph plotting equilibrium concentrations in a titanium tetrachloride and hydrogen system with added argon gas as a function of temperature.

Conditions necessary for complete dissociation of $TiCl_4$ can be predicted using free energy minimization techniques which assume thermodynamic equilibrium. FIG. 4 shows the species as a function of temperature for a $TiCl_4+2H_2$ system at 1 atm. When argon is taken into account (to 96%) there is basically no change in the relative species distribution. As seen in FIG. 4, as $TiCl_4$ is heated the chlorides are stripped off, until at temperatures above 5000 K there is a substantial amount of only Ti, $Ti^+$, Cl, $Cl^-$, TiCl, HCl and $H_2$. However as the amount of hydrogen, relative to that required for a stoichiometric HCl product, is increased to 32:1 this diagram shifts to lower temperatures (FIG. 5). In all cases the requirement is for good mixing and a sufficient residence time of the reactants in the plasma.

Homogeneous (gas phase) nucleation of particles from the vapor in a plasma system has been studied theoretically and published discussion of such issues are readily available. The initiation of homogeneous nucleation depends on the formation of small atom clusters which arise due to collisions. Normally, the cluster evaporation rate is much greater than the condensation rate and the particle clusters do not grow. However at sufficiently low temperatures the vapor becomes supersaturated and the condensation rate drastically increases. This results in a nucleation burst after which time the particles increase in size slowly.

In a rapidly cooling plasma system one can think of the gas in equilibrium at temperature $T_0$ and pressure $P_0$ being suddenly quenched in temperature and pressure. For Ti—Cl—H at 6000 K, published results estimate a chemical equilibration time of less than 10 nsec. At this temperature the reactants should be well equilibrated. As the plasma cools this characteristic time increases until at a particular T and P, the cooling rate becomes greater than the equilibrium rate and the composition of the plasma is "frozen." On further temperature decrease, the vapor pressure of one component subsystem becomes greater than the saturation vapor pressure and nucleation occurs. When this subsystem is charged, condensation is enhanced for that species.

Taking into consideration the free energy equilibrium condition shown in FIG. 4, in order to avoid stable $TiCl_x$, x=2, 3, 4 compounds, the gas must be frozen at temperatures above 5000 K. With an overabundance of hydrogen this temperature can be reduced to about 3000 K (FIG. 5). Freezing the mixture at even lower temperatures will result in a substantial amount of $TiCl_x$ vapors. However, if the vapor pressure of these subchlorides never gets above saturation, they will not condense. Hence, it is possible to extend the equilibrium reactor chamber temperature down to lower temperatures. This will result in some loss of Ti in the form of gas subchlorides. It is clear from this that a higher temperature quench will result in a better yield of the desired end product.

The saturation vapor pressures of Ti—Cl compounds at all temperatures are greater than that of Ti, and it is possible to selectively condense Ti metal. The presence of hydrogen serves to isolate the titanium from the chlorine atoms by forming both HCl and TiH in the gas phase.

Experimental conditions for selective condensation of Ti from a Ti—Cl—H—Ar plasma depend on specific values of rate coefficients and upon the initial temperature and pressure $T_0$ and $P_0$ at which the plasma is frozen. The product is also dependent on the cooling rate of the plasma and upon the geometry of the reactor. Of course not all reaction pathways become "frozen" at the same temperature during quench.

The converging-diverging nozzle configuration used in supersonic flow applications offers possibilities to control both the temperature quench rate and the concentration at which the plasma becomes "frozen" during the expansion. The converging-diverging DeLaval nozzle and the associated Prandtl-Meyer expansion process are discussed in standard texts on compressible fluid flow. In such expansion nozzles the hot plasma gas undergoes an approximate isentropic expansion and the energy in the gas (its enthalpy) is converted to unidirectional velocity in the diverging nozzle. When the exit pressure is sufficiently low, it is possible to reach supersonic speeds. Non-adiabatic expansion processes which are attained in practice aid in the resultant temperature search.

A number of preliminary experiments with $TiCl_4$ gas injected into an argon or argon-hydrogen plasma have been completed. The dimensions and geometry of the reactors have been varied. Provisions were made for gas quenching at the throat exit. The production of substantial amounts of fine (<100 nm) metal powders over a wide range of parameters has been successfully accomplished.

Nitrogen gas impurities in such systems result in the formation of solid $NH_4Cl$ powder which can be separated from the (black) powder produced by heat treating at about 400° C. in flowing hydrogen. Oxygen impurities, however, result in $TiO_2$ production. In virtually all runs to date, the only chlorine in the final product is that tied up as ammonium chloride and the product can be upgraded to be chlorine free. Presently HCl is condensed in a cold trap placed just before the downstream pumping system.

The powder produced is black. The as-produced product has been analyzed by SEM and characterized by Energy Dispersion Spectra (EDS). A SEM scan of the powder showed finer structure. A typical x-ray diffraction (XRD) scan is featureless (flat). It shows no crystal structure nor any short range ordering. An electron diffraction pattern confirms this result. The maximum yield of titanium metal to date with the present system is 5 gm/hr. It is 100% free of chlorine.

The addition of hydrogen to the plasma system ties up the chlorine atoms and produces TiH powder. The presence of hydrogen allows the powder to be relatively easily handled and may be crucial to scaled-up metal production facilities. When the powder is left in air for a few weeks, it turns noticeably white, indicating oxidation of the metal. In-situ laser induced fluorescence of TiO has been observed in the expansion chamber with a small amount (~100 ppm) of oxygen in the Ar carrier gas. This fluorescence can serve as a diagnostic to investigate temperatures in the expansion zone.

The described apparatus and method have been successfully tested with respect to production of powdered titanium metal. Product yields have exceeded 80% of theoretical yields. Analysis has confirmed that the produced powder is titanium metal and consisted of partly agglomerated submicron particles. Submicron powder production has been consistent from one run to the next. Laboratory experiments have successfully produced up to 5 grams of titanium per hour, which is to be compared to CVD deposition rates in the order of tenths of a gram of titanium per hour.

EXAMPLE 2

Titanium Dioxide $TiO_2$ production in the 50 nm range can also be carried out in the existing facilities. For this purpose, $TiCl_4$ is injected into an argon plasma and mixed with $O_2$ just before the quench zone. Most of the $TiO_2$ produced today is used in the paint industry and a 50 nm size (rather than the present 200 nm) is advantageous. There is also some interest in fine $TiO_2$ as a ceramic. Preliminary results at low $TiCl_4$ (~1 gm/hr) flow are encouraging.

The resulting titanium dioxide has a rutile structure, which has superior properties in blocking ultraviolet light. Titanium dioxide particles can be produced with average diameters of 10 nanometers or less in the narrow size ranges as defined, which can find use as a sun blocking agent for protecting human skin against harmful effects of sunlight.

The process meets all requirements for titanium production, in that it provides downstream reduction in a kinetically controlled reactor to remove halide from back reactions, leaving free metal in the exiting gaseous stream. Unwanted atomic reactions cannot occur in the reactor due to the short residence time of the gaseous stream.

EXAMPLE 3

Acetylene

Methane conversion to acetylene in a high temperature reactor follows the theoretical chemical reaction: $2CH_4 \rightarrow C_2H_2 + 3H_2$. In principle, under careful kinetic studies on the pyrolysis of methane it has been shown that it is possible to obtain high yields of acetylene where the main by-product is hydrogen, instead of tars and acetylene black. Such studies also showed that pyrolysis in the presence of hydrogen suppressed carbon formation.

In practice, a range of other hydrocarbons, specifically the light olefins and solid carbon, are always formed as byproducts with acetylene if the reaction condition is not well controlled. Equilibrium thermodynamic calculations predict a yield of acetylene at 38%, but plasma conversion experiments indicate acetylene yields are as high as 70–85%. Solid carbon formation can be as low as 10%.

Experiments using the fast quench system of this disclosure have revealed that the methane decomposition to acetylene is kinetics controlled rather than equilibrium controlled. These results point to the advantage of high quench rates which provide opportunities to preserve high temperature equilibrium products.

Figure 6:
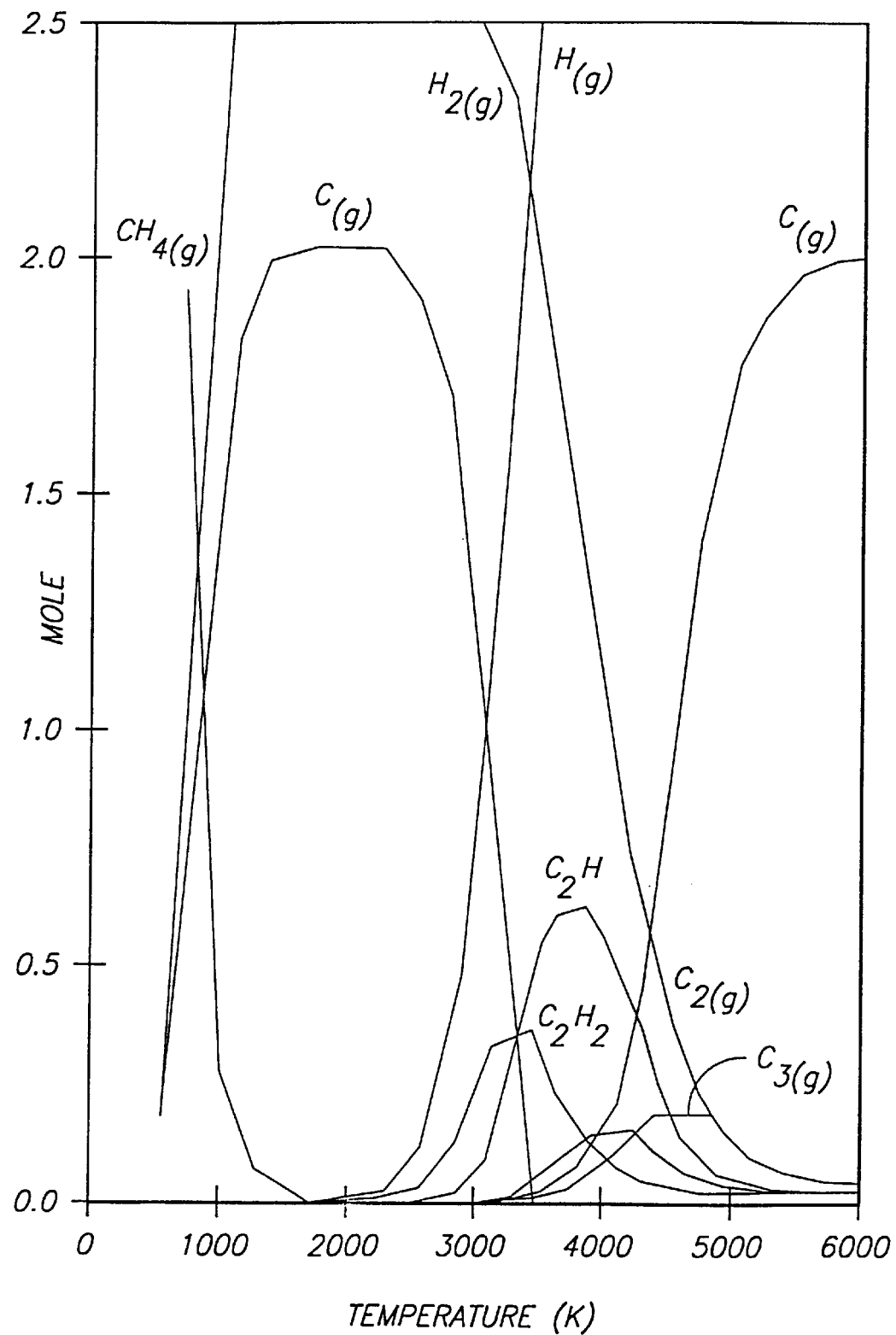
FIG. 6 is a graph plotting equilibrium concentrations in a methane decomposition system with solid carbon precipitation.
Figure 7:
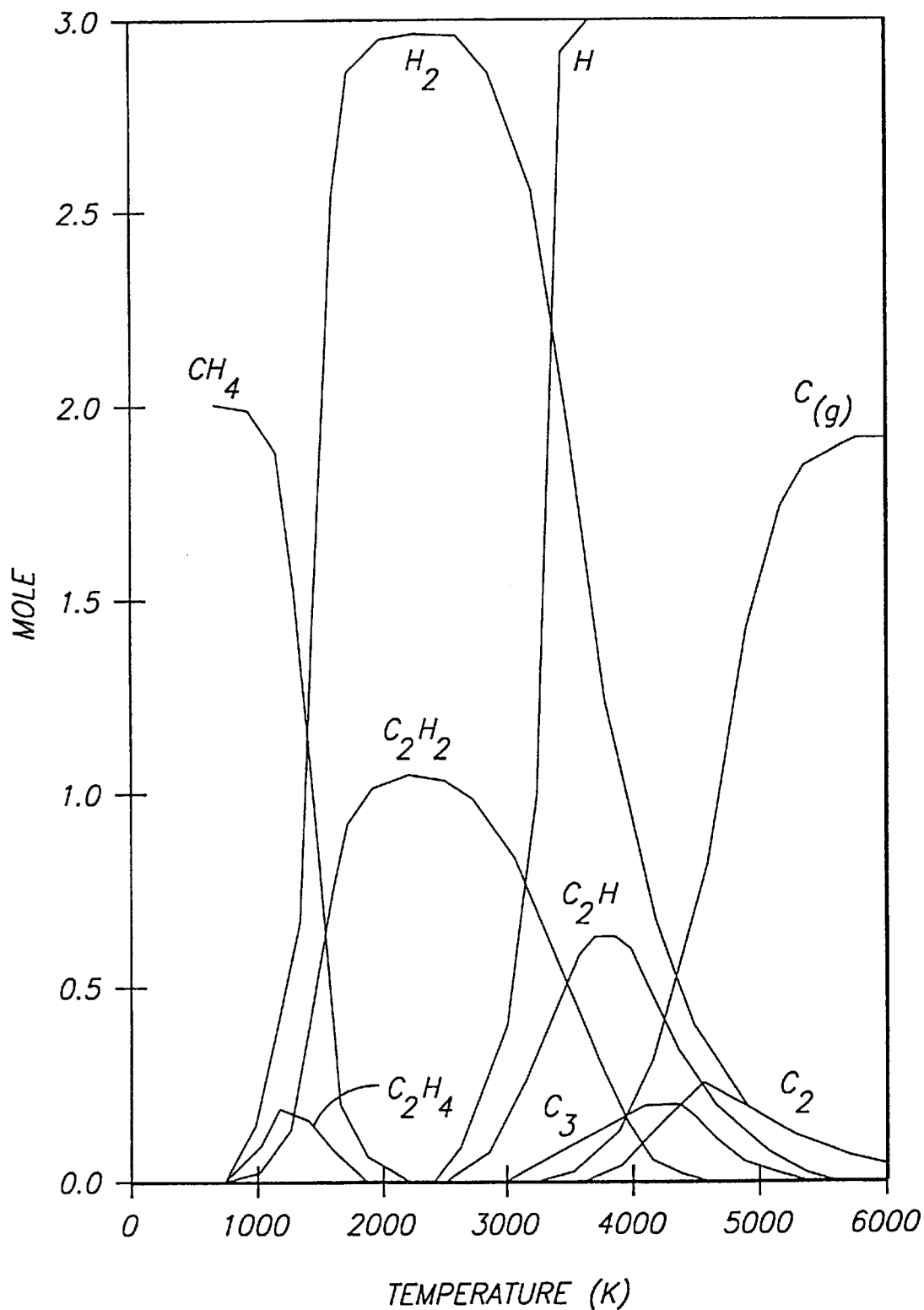
FIG. 7 is a graph plotting equilibrium concentrations in a methane decomposition system with solid carbon precipitation prevented.

FIGS. 6 and 7 respectively show the equilibrium compositions of methane conversion to acetylene with (FIG. 6) and without (FIG. 7) solid carbon nucleation in the reaction. It is clearly seen from these results that if $C_2H_2$ is allowed to 'slowly' reach equilibrium at low temperatures it will decompose to acetylene black. Therefore, to maximize acetylene formation, the nucleation of solid carbon from acetylene must be suppressed at all temperatures. From classical nucleation theory, the nucleation rate, $I_i$, of solid carbon from a supersaturated hydrocarbon vapor species i is given by:

$$I_i = I_0 \left( \sigma^{1/2} \left( \frac{P_i}{T} \right) \right)^2 \exp\left( -\frac{16\pi\sigma^3 v^2}{3kt(kT\ln SS)^2} \right)$$

where $\sigma$ is surface tension, $P_i$ is the vapor pressure of species i, and v is the molecular volume of species i. SS, a ratio of $P_i/P_\infty$, is the supersaturation of species i with its solid at temperature T. In SS is the degree of supersaturation of the vapor pressure of species i at the specific temperature T.

The homogeneous nucleation of carbon solid from the supersaturated hydrocarbon vapor species i occurs by the following sequence of events:

1. The gas-phase reaction proceeds until the supersaturation exceeds a certain critical value ($>10^5$ or In SS$\geq$5).
2. The nucleation occurs like a burst over a relatively short time period ($10^{-6}$s).
3. The nucleation terminates due to the loss of nucleating species in the gas phase which are depleted by diffusion to the freshly formed particles.

From the equation above, it is clear that the degree of supersaturation from the chemical species controls the byproduct carbon nucleation from the gas phase reaction. Calculation of In SS will indicate the most probable carbon precipitation mechanism.

One prior published report fed methane into the flow of an argon plasma jet, and the experimental results showed about 80% acetylene was formed in the reaction. On the contrary, thermodynamic equilibrium calculations predicted a $C_2H_2$ composition of 38% in equilibrium with solid carbon. The result indicated acetylene is a high temperature metastable compound and that it will decompose to "acetylene black" if the gas is allowed to reach low temperature equilibrium slowly. Table 2 illustrates the dependence of C(s) nucleation on the magnitude of In SS by some of the participating reactions. On the other hand, if solid carbon formation could be prevented, then the equilibrium calculation (FIG. 7) showed acetylene would be the favored product over a much wider temperature range. This calculation demonstrates that if the kinetics of methane pyrolysis reaction can be controlled, the yield of $C_2H_2$ can be maximized at the theoretical reaction. This led to the present attempt to identify the kinetic conditions for quenching the reaction in a manner that carbon solid nucleation from acetylene is prevented.

TABLE 2

| Reaction | Temperature K | Log $K_p$ (or ln SS) |
|---|---|---|
| $C(g) = C(s)$ | 3200 | −0.18 |
| | 3000 | 0.17 |
| | 2800 | 0.59 |
| $½C_2(g) = C(s)$ | 3400 | −1.77 |
| | 3200 | −1.61 |
| | 3000 | 0.41 |
| $⅓C_3(g) = C(s)$ | 3200 | −1.58 |
| | 3000 | 1.39 |
| | 2800 | 2.55 |
| $½C_2H(g) = C(s) + ¼H_2$ | 3000 | 0.86 |
| | 2500 | 1.17 |
| | 2000 | 2.8 |
| $½C_2H_2(g) = C(s) + 1/H_2$ | 2000 | −5.48 |
| | 1500 | −8.28 |

From FIGS. 6 and 7, as well as in Table 2, it can be seen that species such as C(g), $C_2$(g), $C_3$(g), and $C_2$H(g), are not strongly favored for carbon precipitation down to 2000 K. On the other hand, the carbon nucleation rate from $C_2H_2$ is extremely high starting at 2000 K because (ln SS)$^2$ is very large, and acetylene decomposition to acetylene black is favored. Therefore, acetylene will decompose to solid carbon if it is allowed to reach equilibrium "slowly" at temperatures below 2000 K. In order to maximize the acetylene yield, the overall gas temperature after mixing with injected methane must reach a value between 2000–2500 K. It is necessary to quench from these temperatures to <500 K in a very short time to suppress solid carbon nucleation.

As previously stated, the super fast quench phenomena observed in this reactor is achieved by rapidly converting thermal energy in the gases to kinetic energy via a modified adiabatic and isentropic expansion through a converging-diverging nozzle. In the process, the gas temperature and pressure drop extremely fast and the gas reaches supersonic velocity. Acetylene is more stable than other alkanes or alkenes at temperatures above 2000 K. This is a consequence of the fact that the free energy of acetylene decreases at elevated temperatures compared to other hydrocarbons. However, because this window of opportunity is very short-lived (<10$^{-3}$ sec) in a high temperature pyrolysis reactor, to stabilize maximum conversion of acetylene, it is necessary to rapidly cool the emerging gas below 600 K to prevent decomposition to carbon, hydrogen, or acetylene condensation products (tars). To understand the acetylene quench phenomenon in this reactor, it is necessary to investigate the changes in the temperature, pressure, and velocity of the gases as a function of the previously-described changes in reactor geometry.

Assume that the final temperature drops almost by a factor of 4, which is easily attainable through the quench nozzle, if the final temperature in the quench chamber for the acetylene reaction is 500 K, then the initial temperature before the quench nozzle would be around 2000 K. This temperature would be associated with maximum acetylene conversion (FIG. 6), and the nucleation of solid carbon would be suppressed. To achieve maximum $C_2H_2$ yield, the average temperature should be between 2500 to 2000 K after $CH_4$ injection, followed by quenching the gas composition immediately to <500 K to stabilize the acetylene.

Locating the proper temperature zone for maximum $C_2H_2$ formation before quenching is important to minimize solid carbon nucleation. The plasma temperature is very high (>>5000 K) and the plasma gas is very viscous. This temperature will need to be cooled to an average of 2500–2000 K by mixing with injected methane for maximum acetylene yield. To achieve good mixing between methane and plasma gas to reach a uniform average reaction temperature it is necessary to overcome the high viscosity of the plasma gas. The window of opportunity for stabilizing maximum acetylene yield is very narrow and short. Therefore, defining the location of methane injection and position of the nozzle for immediate quenching of the product is extremely important.

In a proof of concept study, a Plasma Fast Quench Reactor was designed and built, utilizing expansive cooling to convert methane to acetylene. It was constructed basically as shown in FIGS. 1 and 2.

Hydrogen was used as a reactive plasma gas to heat methane to reaction temperatures and also served as a suppressant for solid carbon nucleation from the reaction. Downstream in the nozzle region, hydrogen could be used as an optional coolant of the diverging section of the nozzle if it is desirable. Initial experiments of methane conversion based on carbon balances yielded a product, in a single pass, consisting of 71% acetylene, 27% carbon black and 2% ethylene. The product gas also contained hydrogen as a by-product.

The best conversion observed in a series of experiments resulted in a product consisting of approximately 85% acetylene, 10% carbon black, and the balance other hydrocarbon gases. Besides carbonaceous products, hydrogen was also produced as a by product. These limited experiments clearly demonstrated the feasibility of the process and the potential superiority to any of the existing processes. In addition to the high conversion efficiency, the process has other significant features:

The process has a very high selectivity to acetylene production.

The system is very simple and compact, suggesting that capital costs for implementing it will be low.

The converging-diverging nozzle converted thermal energy to kinetic energy. Gas velocity downstream from the nozzle was believed to be supersonic; opportunities to use this kinetic energy to drive a turbine-generator are obvious.

By-product hydrogen could be used as feed stock for other processes or could be burned to drive a turbine generator to provide additional electrical power to the process.

The acetylene can be converted to other high value commodity chemicals by applying established chemical processes down stream of the reactor.

EXAMPLE 4

Other Applications

Table 3 is a condensation of information relating to application of this system to already proven end products. It lists reactants and plasma gas combinations that have successfully produced the identified products.

Since a number of modifications and changes in system configuration, operating set point and gas mixture were required to successfully demonstrate the hydrogen reduction of $UF_6$ to uranium metal a more detailed description is given below. Preliminary problems that had to be solved were an insufficient degree of quenching, caused by less than optimum operation of the supersonic, converging-diverging nozzle, insufficient heat content (enthalpy) and temperature in the plasma gas, and poor mixing of the injected $UF_6$ with the plasma gas.

In order to increase the degree of quenching (by increasing the Mach number at which the converging-diverging nozzle operated the system operating pressure was increased to approximately 40 psi.

Operation of the plasma source (torch) at this elevated pressure on a mixture of argon and hydrogen resulted in poor efficiency (<10% thermal efficiency) low plasma temperature, and energy content (enthalpy). The major source of this inefficiency was radiative heat transfer to the cooled anode. The energy input to the plasma (enthalpy) and resulting plasma temperature at this condition were insufficient to totally dissociate the $UF_6$, a condition that is necessary for successful processing. This problem was corrected by redesigning the torch anode and changing the gas mixture. The redesigned anode was larger in diameter (7 mm) and had a constant area profile. The gas flow rate was increased to stretch the arc resulting in an increased torch voltage and energy input (enthalpy) to the plasma. The plasma gas was changed to a mixture of Ar, He, and $H_2$ in the volume ratio of 65:32.5:2.5 respectively. This also increased the arc voltage and minimized the radiative heat loss from the plasma to the cooled anode thus maximizing both the enthalpy (energy content) and temperature, while still providing sufficient hydrogen for reaction with the fluorine ($F_2+H_2 \rightarrow 2HF$) and the formation of uranium-metal in the condensation region of the nozzle and reactor.

The final problem to be solved was optimization of the injector to insure "good" mixing of the $UF_6$ with the plasma gas. A $UF_6$ feed system which would provide $UF_6$ at controlled temperature (between about 10 and about 100° C.) and elevated pressure (between 40 and about 75 psi) was designed. The $UF_6$ gas was mixed with an argon carrier gas and transversely injected at velocities ranging from 100–600 m/s. Operation of the injector at these velocities and avoidance of injector plugging and erosion required a reduction of the injector orifice size to 1–2.5. The optimum injection was found to be around 200 m/s. This condition resulted in adequate mixing and a successful experiment.

The recombination of the hydrogen and fluorine to form HF has been numerically modeled. The reactions considered are shown below, where M is a collision partner which may include Ar or He.

$$H+H+M=H2(g)+M \tag{1}$$

$$H+F+M=HF(g)+M \tag{2}$$

$$F+F+M=F2(g)+M \tag{3}$$

$$H2F+HF(g)+H \tag{4}$$

$$H+F2=HF(g)+F \tag{5}$$

The first three equations are three—body reactions which proceed at a relatively slow rate as compare with the gas velocity and nozzle transit time. The relative slow rate of these reactions result in elevated non-equilibrium populations of atomic hydrogen and fluorine in the expansion process. The presence of molecular hydrogen plays an important role in the process by rapidly reacting with free atomic fluorine atoms and thus preventing atomic fluorine from attacking elemental uranium and formation of undesirable UFx. Reactions 4 and 5 are two body reactions, which proceed at a rate significantly higher than reactions 1–3. For a completely dissociated mixture the formations of HF is limited by the reaction rates for reactions 1 and 2. The reaction of room temperature uranium metal with molecular $F_2$ and HF is known to be a relatively slow process. The reaction rate for the reaction of uranium metal and atomic fluorine (F) is not currently known but has the potential to be a significant mechanism for formation of uranium fluorides due to the high reactivity atomic fluorine. Initially it was thought that injection of molecular hydrogen at the nozzle exit would be advantageous to remove the atomic fluorine. Subsequent work has demonstrated that injection of molecular hydrogen at the nozzle throat will be even more advantageous. The injection point can be either slightly upstream, down stream, or in the nozzle throat. In the presence of excess molecular hydrogen the two body reactions 4 and 5 proceed quite rapidly to form HF gas which is easily separated from solid uranium particles. The addition of cold molecular hydrogen gas has the added benefit of increasing the quenching of the product mixture by increasing the gas velocity and by thermal cooling of the gas.

It has also been determined that to obtain rapid mixing and heating of metal halide reactants in the plasma, that optimum mixing and heating occur when the reactant is in the gas phase and has an injection velocity of 50 to 300 meters per second with the preferred injection velocity of 100 to 300 meters per second. This if for reactant injection normal (90 degrees) to the plasma gas flow.

TABLE 3

| Reactants | Plasma Gas | Injection Method | Injection Position | C-D Nozzle Shape (angle) | Products |
|---|---|---|---|---|---|
| $TiCl_4 + H_2$ | Argon/ Hydrogen | $TiCl_4 + H_2$ @ 180–200° C. | 3.0–6.0 mm from Torch exit | C-45° to bell shaped D-25-6° | Titanium Metal + HCL gas |
| $VCl_4 + H_2$ | Argon/ Hydrogen | $VCl_4 + H_2$ @ 180–200° C. | same as above | same as above | Vanadium Metal + HCl gas |
| $AlCl_3 + H_2$ | Argon/ Hydrogen | $AlCl_3 + H_2$ @ 120–150° C. | same as above | same as above | Aluminum Metal + HCL gas |
| $TiCl_4$ + $VCl_3$ (or $VCl_4$) + $H_2$ | Argon/ Hydrogen | $TiCl_4/VCl_{3\ or\ 4}$ + $H_2$ @ 180–200° C. | same as above | same as above | TiV Alloy powder + HCl gas |
| $TiCl_4$ + $BCl_3$ + $H_2$ | Argon/ Hydrogen | $TiCl_4$ (liq) @ 50 psi + $BCl_3$ (gas) @ 50 psi + $H_2$ | same as above | same as above | $TiB_2$ composite Ultrafine powder ceramic |

TABLE 3-continued

| Reactants | Plasma Gas | Injection Method | Injection Position | C-D Nozzle Shape (angle) | Products |
|---|---|---|---|---|---|
| $TiCl_4 + O_2$ | Argon/ Oxygen or Oxygen | $TiCl_4$ (liq) @ 50 psi + $O_2$ (gas) @ 50 psi | $TiCl_4$ (liq) 1–3 mm from torch exit | C-Bell Shaped D-10 to 25° included | Ultrafine $TiO_2$ ceramic powder |
| $WF_6 + H_2$ | Argon/Hydrogen/or Hydrogen | $WF_6$ (g) @ 50 psi, 80–120° C. | $WF_6$(g) at torch exit | C-Conical D-Conical 10–20° included | Ultrafine Tungsten Metal powder |
| $UF_6 + H_2$ Argon | Argon/Hydrogen/Helium | $UF_6$ (g) @ 40–75 psi, 20–100° C. | $UF_6$ (g) at torch exit | C-Conical D-Conical 10–20° included | Ultrafine Uranium metal powder |
| $H_2 + CH_4$ | Argon/ Hydrogen or Hydrogen | $CH_4$ (gas) @ 50–100 psi | interior of torch or 1–3 mm from torch exit | C-Bell Shaped D-10 to 25° included | 80% + Acetylene Lesser amounts of ethylene & carbon (s) |
| Argon + $CH_4$ | Argon | $CH_4$ (gas) @ 56–100 psi | Interior of torch or 1–3 mm from torch exit | C-Bell shaped D-10 to 25° included | Ultrafine carbon black powder |

One very important commercial product listed in Table 3 is the ultrafine titanium dioxide ceramic powder obtained by oxidizing titanium tetrachloride in an oxygen enriched plasma gas. This system has been successfully used to produce an ultrafine particle size range of less than 500 nanometers, with 10–100 nanometers being the preferred range. The particles have been successfully produced within a narrow size range, meaning that 90 percent of the particles would fall within a 25 nanometer size range.

Laboratory Tests

An initial experiment to produce titanium metal powder was successfully conducted using the plasma fast quench process early in the development of this system. A nontransferred plasma torch was operated at 3 kW input power. Argon was bubbled through liquid titanium tetrachloride and the argon with entrained titanium tetrachloride vapor was injected into the argon plasma jet at the torch exit. Hydrogen reductant was injected normal to the plasma at a position 180° and directly across from titanium tetrachloride injection.

The reaction chamber, converging/diverging nozzle and downstream cooling section were constructed of copper coated with an alumina type ceramic. The purpose of the ceramic was to prevent corrosion of the cooper by HCl produced in this process and reduce heat loss from the reaction zone.

The reactor chamber for this original system test was 2.0 cm in diameter by 10.0 cm in length. The quench section consisted of a 90° included angle converging section followed by a 3.0 mm diameter throat and a 90° included angle diverging section issuing into a 4.0 cm diameter by 20 cm long cool down section. Four tangential hydrogen gas jets (1.0 mm diam) were placed in the diverging section of the nozzle approximately 5 mm downstream from the nozzle throat. Injection of cold hydrogen gas at this point seemed to improved yields of titanium. It was later learned that even better quenching could be accomplished by reducing the expansion angle of the diverging section of the nozzle to less than a 20° included angle, with the optimum diverging included angle being 6° to 14°.

As a further example of dimensional design for a laboratory-scale reactor, subsequent tests were conducted using a reactor chamber length of 20 mm, although tests have been conducted with reactor chamber lengths ranging to 150 mm lengths. The plasma inlet opening was 6 mm and the reactor chamber interior diameter was 11 mm. The downstream cool down section after the nozzle was typically 1 to 1.3 m, although lengths ranging from 0.3 to 4 m have been tested. The cool down section can be constructed as long as required to reach a desired final temperature in the exiting gaseous stream and products contained within it.

The system used for proof of concept experiments was based on relatively crude approximations of anticipated velocity, pressure, and temperature profiles. While formation of carbon black is of concern because it reduces yield, this can be minimized by experimentally determining the optimum location of quenching. Similarly, the choice of materials of construction for this equipment can be important, as certain materials catalyze undesirable reactions or conversely can catalyze the desirable reactions.

Titanium metal powder production in the early laboratory device was on the order of 0.1 to 0.5 grams per hour. This yield was improved to 0.5 to 1.0 gram per hour by (1) optimizing the geometry of the reactor; (2) addition of 1 to 5% hydrogen to the argon plasma gas to increase heat to the process while also preheating the hydrogen reductant for reaction with titanium tetrachloride; (3) injecting liquid or vaporized titanium tetrachloride into the reaction zone with a minimum of carrier gas; and (4) use of hydrogen as the carrier gas.

The quench reaction zone geometry was optimized by conducting two dimensional modeling of the fluid dynamics of such a system. Modeling results determined that reaction zone diameter should be no larger than 200% of the plasma torch anode exit diameter with the optimum being 110% to 150%. This prevents recirculation of reaction gases in the reaction zone which would contribute to undesirable side reactions and decrease product yields.

Gas temperatures were measured experimentally along an elongated reaction section and were also modeled using a two dimensional fluid dynamics model to determine the optimum length of the reaction zone before the converging section. A reaction zone length was chosen from this data for a given plasma input power level, plasma gas flow, and reactant input rate which would result in gas temperatures at the entrance to the nozzle throat to be greater than the required equilibrium temperature of the desired end product—4000 K (for production of titanium).

A high aspect ratio converging section was designed such that the radius of the convex and concave surfaces leading into the nozzle throat were approximately equal to the diameter of the nozzle throat. This converging geometry allows achieving the highest possible velocity at the entrance to the nozzle throat while limiting heat loss to the walls of the converging section or separation of the gas flow from the converging surface.

The optimum area (diameter) of the nozzle throat was calculated from equations available in texts pertaining to nozzle design. The nozzle throat was designed so that with the temperature, gas composition, mass flow, and pressure of the gas entering the nozzle known (or estimated) sonic or near sonic gas velocities are achieved in the nozzle throat. To achieve maximum cooling (temperature drop) the nozzle throat should be as short as possible. This is demonstrated by two equations for two-dimensional nozzle flow, with $R^*$ and $h^*$ designating the radius of curvature and throat height respectively:

$$\left[\frac{d\left(\frac{T}{T_o}\right)}{dt}\right]^* = -(R^*h^*)^{1/2}\frac{\gamma-1}{\left(\frac{\gamma+1}{2}\right)^2}a_o$$

$$\left[\frac{d\left(\frac{T}{T_o}\right)}{dt}\right]^* = -C(a_o(R^*h^*))^{-1/2}$$

where $T_0$ and $a^o$ are the gas temperature and speed of sound respectively in the reaction zone. In the second equation above, all constants for a given gas are collected in C. for air (gamma=7/5 or 1.4, C=0.278). Examination of these equations shows that greater cooling rates occur for smaller nozzle diameters and shorter nozzle lengths with generally smaller $R^*$ and $h^*$.

The divergence angle and area at the exit of the diverging nozzle were determined from standard texts on fluid dynamics and aerospace rocket motor design. In addition, two dimensional models of fluid flow under expected experimental conditions were also used to optimize the divergence angle and exit area of the nozzle. It was concluded that the optimum divergence included angle was less than 35° and preferably in the range of 10° to 14° for optimum expansion and acceleration of the gas. The maximum exit area (diameter) of the diverging nozzle was again determined by calculation from equations available in standard texts on fluid flow and rocket engine design.

The maximum allowable nozzle exit area depends on the mass flow through the nozzle and pressure difference between the reaction zone and the downstream cooling section. Choice of too large an expansion angle or too large an exit area will result in the gas flow "peeling off" or separating from the wall, which results in the undesirable conditions of turbulence, gas recirculation, gas reheating, and side or back reaction degradation of the desired end products.

The purpose of the cool down section of the plasma fast quench reactor device is to reduce the gas velocity while removing heat energy (which results from the decrease in velocity) in the gas at a rate sufficient to prevent the gas from increasing in kinetic temperature. Passage of the gaseous stream through the restrictive nozzle opening reduces its kinetic temperature, but remove no energy from the gas. The exiting gaseous stream is slowly warmed as some random motion of the gaseous contents is restored. This heat must be immediately removed from the system as it is produce, thereby maintaining the kinetic temperature of the resulting gaseous stream at a desired equilibrium level and preventing back reactions downstream from the nozzle.

In the case of experimental work to date this "cool down" has been accomplished by the use of length of water cooled tube having the same internal diameter as the internal exit diameter of the diverging section of the nozzle. With other applications of this device, it may be more desirable to supplement gas cooling by use of other types of heat exchangers.

Plasma quench processes for production of ultrafine materials require product collection capability downstream of the quench nozzle, preferably downstream of the cool down section. Bench scale experiments to date have used cyclonic collectors of standard dimensions described in the literature for gas and mass flows several time smaller than called for in the literature. This accommodates sonic or near sonic gas velocities through the cyclones, which allows efficient removal of ultrafine material (10 to 50 nm diameter powders).

In addition to mass flow and nozzle diameter, the third process parameter that determines the temperature drop across the nozzle is the ratio of the up stream pressure ($P_0$, in reaction zone) to the downstream pressure ($P_1$, cool down zone). In bench scale tests for the production of titanium metal powder and other materials, the ratio $P_0/P_1$ of 0.01 to 0.26 was maintained. The experimental systems were operated with the reaction zone pressure of approximately 700 to 800 Torr (ca. 1 atm.) and downstream pressure maintained between 10 and 200 Torr (0.26 to 0.01 atm.). In bench scale experiments, the low downstream pressure was accomplished using a mechanical vacuum pump.

For large scale production of ultrafine powders, it is expected that the quench system would be designed to operate with elevated pressures in the plasma torch and reaction chamber of 5 to 10 atmospheres pressure. This would accomplish the desired pressure drop across the nozzle while reducing or possibly eliminating the need for a vacuum device to lower the pressure on the downstream side of the nozzle.

Using design considerations given in the section above and equations outlined in published texts relating to nozzles, a bench scale reactor was constructed for synthesis of titanium, vanadium, aluminum, and Ti/V Alloys. This equipment was designed for operation at 12 KW input power to the plasma torch, using a plasma gas flow of 50 scfh and a plasma gas made up of 95% argon and 5% hydrogen gas. The equipment used to produce these materials consisted of a small bench scale plasma torch operated at 12 kW electrical input power attached to a reactor section, quench nozzle, cyclone powder collector, liquid nitrogen cold trap to collect by-product HCl, and mechanical vacuum pump.

To produce titanium metal particles, titanium tetrachloride was heated above its boiling point and injected into the reaction chamber at the junction between the plasma torch and the reaction section. The reaction section, quench nozzle, and expansion chamber were constructed of water cooled nickel. The reaction section was 11.0 mm inside diameter and 150.0 mm in length. The quench nozzle section consisted of a high aspect ratio converging section followed by a 6.2 mm nozzle, and 12° included angle expansion section followed a 20.0 mm I.D., 50.0 cm cool down section. The cooled mixture of titanium powder and gas was passed through two sonic cyclone particle separators to collect the ultrafine powder. Hydrogen chloride vapor was condensed out in a liquid nitrogen cooled cold trap to prevent damage to the mechanical vacuum pump down stream from the particle collection. Titanium was produced according to equation (1) below:

$$TiCl_4(g)+2H_2(g)+T>3000° C. \rightarrow Ti(s)+2HCl(g)$$

Ultrafine vanadium metal powder was produced using the bench scale apparatus described above. Vanadium tetrachloride liquid (B.P. 145° C.) was heated to vapor and injected in the same manner as titanium tetrachloride described above with hydrogen carrier gas. Ultrafine vanadium metal powder was produced at the rate of a 0.5 gram per hour according to one of the following equations:

$$2VCl_3(g)+3H_2(g)+T>3000° C. \rightarrow 2V(s)+6HCl(g)$$

$$VCl_4(g)+2H_2(g)+T>3000° C. \rightarrow V(s)+2HCl(g)$$

An ultrafine powder consisting of an alloy of titanium and vanadium was produced by two methods. Method 1 used a mixture of solid vanadium trichloride dissolved in liquid titanium tetrachloride. This mixture was then heated to vapor and injected into the plasma quench reactor in the same manner as with titanium above. In Method 2, vaporized liquid vanadium tetrachloride and vaporized liquid titanium tetrachloride were injected into the plasma quench reactor using separate injectors located in the same axial position but 180° apart on the circumference of the reactor. The chemical equations used are:

$$10TiCl_4(g)+2VCl_3(g)+23H_2(g)+T>3000° C. \rightarrow 10Ti(s)+2V(s)+46HCl(g)$$

$$5TiCl_4(g)+VCl_4(g)+12H_2(g)+T>3000° C. \rightarrow 5Ti(s)+V(s)+24HCl(g)$$

Ultrafine aluminum metal powder was produced by vaporizing (subliming) solid aluminum trichloride in a specially designed oven and carried into the plasma quench reactor in a stream of hydrogen gas in the manner described for titanium above. Special care was needed to insure all sections of the injection system were maintained above 200° C. to prevent formation of solid aluminum trichloride. The process utilized the following equation:

$$AlCl_3(g)+3H_2(g)+T>3000° C. \rightarrow 2Al(s)+6HCl(g)$$

In compliance with the statute, the invention has been described in language more or less specific as to the experimental equipment and methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

Figure 8:
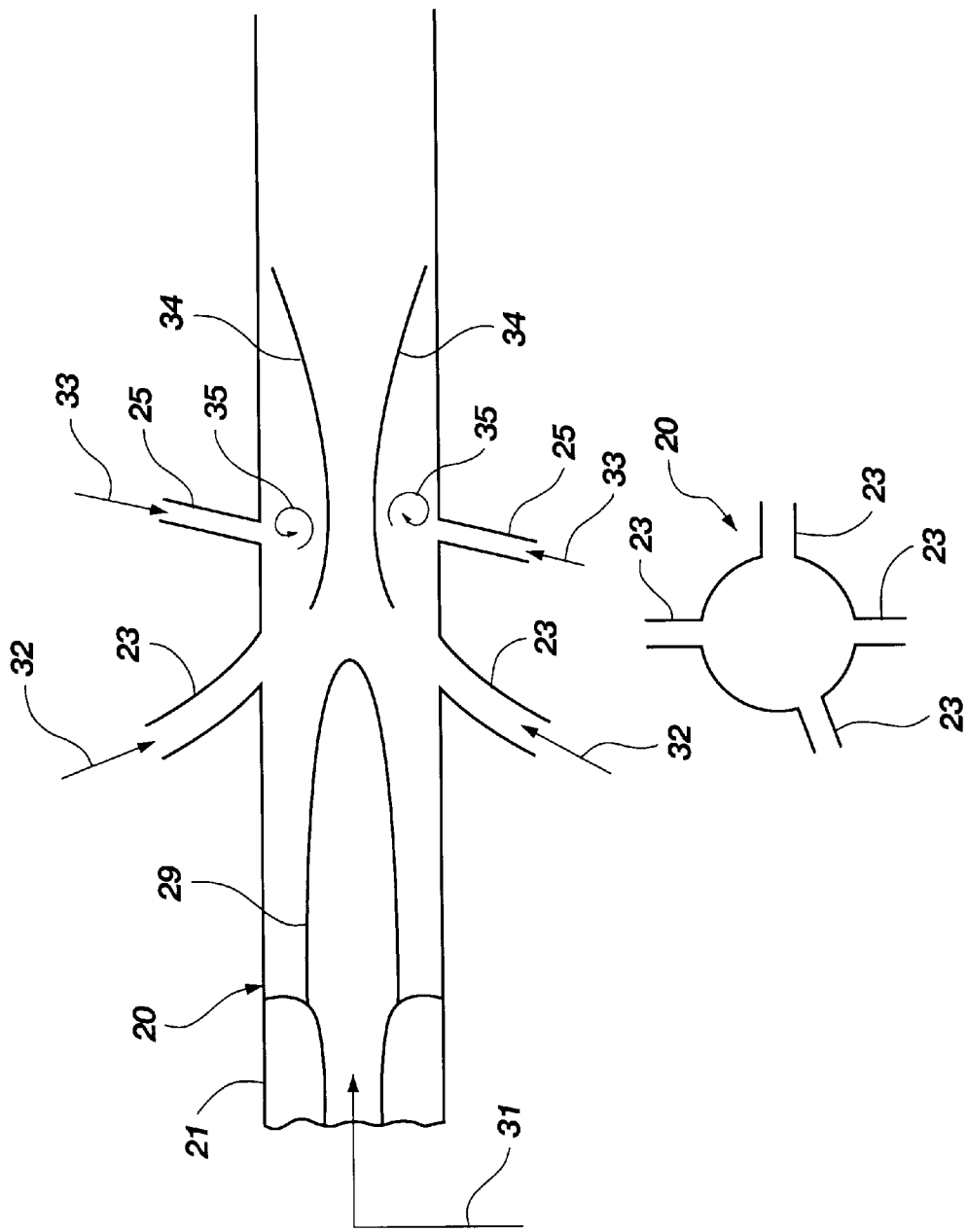
FIG. 8 are side and top cross sectional views of a reaction chamber having a nozzle having two or more supply inlets.

FIG. 8 shows a reaction chamber 20 having a virtual convergent-divergent nozzle. The chamber 20 has a plasma gas 31, plasma arc 21, and resulting plasma similar to FIG. 1. Supply inlets 23 focus the incoming reactant streams 32 so as force the reactants toward the center of the reaction chamber 20. The plasma gas 31 and reactant streams 32 as they come together produce an expansion of the reactant stream toward the outlet end of reaction chamber 23 to produce flow lines 34 with flow impedence 35. This expansion results in rapid cooling of the reactants. Supply inlets 25 allow reactant streams 33 containing for example a reducing gas, such as hydrogen, to prevent back reactions and enhance the virtual nozzle effect and the production of the desired product.

We claim:

1. A method for thermally converting one or more metal halide reactants in a thermodynamically stable high temperature gaseous stream to a desired end product in the form of a gas or ultrafine solid particles, comprising the following steps:

introducing a metal halide reactant stream at one axial end of a reaction chamber;

introducing a reducing gas to the gaseous stream prior to or at the time the metal halide reaches a selected reaction temperature;

the reactor chamber having a predetermined length sufficient to effect heating of the gaseous stream to the selected reaction temperature at which a desired end product is available as a thermodynamically unstable reaction product at a location adjacent the outlet end of the reactor chamber;

rapidly expanding the reactant stream to rapidly cool the gaseous stream by converting thermal energy to kinetic energy as a result of adiabatic and isentropic expansion as the reaction stream expands;

adding additional reducing gas to the reactant stream after it has reacted with the initial reducing gas to minimize back reactions, thereby retaining the desired end product within the flowing gaseous stream; and collecting the desired end product.

2. The method of claim 1, wherein the reducing gas is hydrogen.

3. The method of claim 1, wherein the rapid heating step is accomplished by introducing a stream of plasma arc gas to a plasma torch at the one axial end of the reactor chamber to produce a plasma within the reaction chamber which extends toward its remaining axial end.

4. The method of claim 3, wherein the step of rapidly cooling the desired end product is accomplished by use of a restrictive convergent-divergent nozzle.

5. The method of claim 2, wherein the desired end product is titanium metal and the reactant is titanium tetrachloride.

6. The method of claim 2, wherein the desired end product is vanadium metal and the reactant is vanadium tetrachloride.

7. The method of claim 2, wherein the desired end product is aluminum metal and the reactant is aluminum chloride.

8. The method of claim 2, wherein the desired end product is a titanium-vanadium alloy and the reactants are a mixture of titanium tetrachloride and vanadium tetrachloride.

9. The method of claim 2, wherein the desired end product is a titanium-boron composite ceramic powder and the reactants are titanium tetrachloride and boron trichloride.

10. The method of claim 2, wherein the desired end product is uranium and the reactant is uranium hexafluoride.

11. The method of claim 4, wherein the desired end product is uranium, the reactant is uranium hexafluoride, and the reducing gas is hydrogen.

12. The method of claim 11, wherein the first introduction of reducing gas to the gaseous stream is prior to or at the time of the injection of the uranium hexafluoride.

13. The method of claim 12, wherein the step of adding additional reducing gas to the reactant stream is immediately before the nozzle throat, at the nozzle throat, or immediately after the nozzle throat.

14. A method for thermal conversion of one or more metal halide reactants in a thermodynamically stable high temperature gaseous stream to a desired end product in the form of a gas or ultrafine solid particles, comprising the following steps:

introducing a stream of plasma arc gas between the electrodes of a plasma torch including at least one pair of electrodes positioned at the inlet end of an axial reactor chamber, the stream of plasma arc gas being introduced at a selected plasma gas flow while the electrodes are subjected to a selected plasma input power level to produce a plasma within the reactor chamber and extending toward its outlet end;

thoroughly mixing an incoming reactant stream into the plasma by injecting at least one metal halide reactant into the reactor chamber at or adjacent to its inlet end at a selected injection angle and at a selected reactant input rate to progressively effect heat transfer between the plasma and the resulting gaseous stream as it flows axially toward the outlet end of the reactor chamber;

introducing a reducing gas to the plasma arc gas stream prior to or at the time the metal halide reactant stream is added;

the length of the reactor chamber being sufficient to effect heating of the gaseous stream to a selected equilibrium temperature at which a desired end product is available as a thermodynamically unstable reaction product within the gaseous stream at a location adjacent to the outlet end of the reactor chamber;

directing the gaseous stream through a coaxial convergent-divergent nozzle positioned in the outlet end of the reactor chamber to rapidly cool the gaseous stream by converting thermal energy to kinetic energy as a result of adiabatic and isentropic expansion as it flows axially through the nozzle, the nozzle having a converging section and a diverging section respectively leading to and from a restrictive open throat;

adding additional reducing gas to the reactant stream immediately prior to the throat of the nozzle, at the throat of the nozzle or immediately after the throat of the nozzle to minimize back reactions and retain the desired end product in the flowing gaseous stream;

cooling the gaseous stream exiting the nozzle by reducing its velocity while removing heat energy at a rate sufficient to prevent increases in its kinetic temperature; and separating desired end products from the gases remaining in the cooled gaseous stream.

15. The method of claim 14, further comprising the following step:

accelerating the gaseous stream rapidly into the nozzle throat while maintaining laminar flow by passage of the gaseous stream through a converging section of the nozzle having a high aspect ratio.

16. The method of claim 14, further comprising the following step:

controlling the residence time and reaction pressure of the gaseous stream in the reactor chamber by selection of the size of the restrictive open throat within the nozzle.

17. The method of claim 14, wherein the reducing gas is hydrogen.

18. The method of claim 17, wherein the desired end product is uranium and the reactant is uranium hexafluoride.

19. The method of claim 17, wherein the desired end product is titanium and the reactant is titanium hexafluoride.

20. A method for producing titanium, comprising the following steps:

decomposing a titanium compound by introducing two or more reactant streams of titanium compound and one or more other reactants into the same point in a hot plasma in a reaction chamber, such that the reactants react generally at a common point; and rapidly expanding the reactant stream to effect cooling of the reactant stream as the reactant stream moves down the reactant chamber.

21. The method of claim 20, wherein the other reactant is hydrogen and the titanium compound is titanium tetrachloride.

22. The method of claim 21, wherein additional hydrogen is added to the reactant stream after it begins to expand to minimize back reactions and retain the desired end product in the reactant stream.

23. A method for thermally converting one or more reactants in a thermodynamically stable high temperature gaseous stream to a desired end product in the form of a gas or ultrafine solid particles, comprising the following steps:

introducing a reactant stream at one axial end of a reaction chamber;

the reactor chamber having a predetermined length sufficient to effect heating of the gaseous stream to a selected reaction temperature at which a desired end product is available as a thermodynamically unstable reaction product at a location adjacent the outlet end of the reactor chamber;

passing the gaseous stream through a virtual convergent-divergent nozzle formed by directing one or more streams of particles, droplets, liquid or gas into the main flow stream of the reaction chamber to cause the main gaseous stream to flow as if a real convergent-divergent nozzle were present, to rapidly cool the gaseous stream by converting thermal energy to kinetic energy as a result of adiabatic and isentropic expansion as the reaction stream expands; and collecting the desired end product.

* * * * *

UNITED STATES PATENT AND TRADEMARK OFFICE
CERTIFICATE OF CORRECTION

PATENT NO. : 5,935,293  
APPLICATION NO. : 09/076922  
DATED : August 10, 1999  
INVENTOR(S) : Brent A. Detering et al.

It is certified that error appears in the above-identified patent and that said Letters Patent is hereby corrected as shown below:

In the drawings:
In FIG. 1, delete lower right-hand occurrence of reference numeral "29" and associated lead line as shown below.

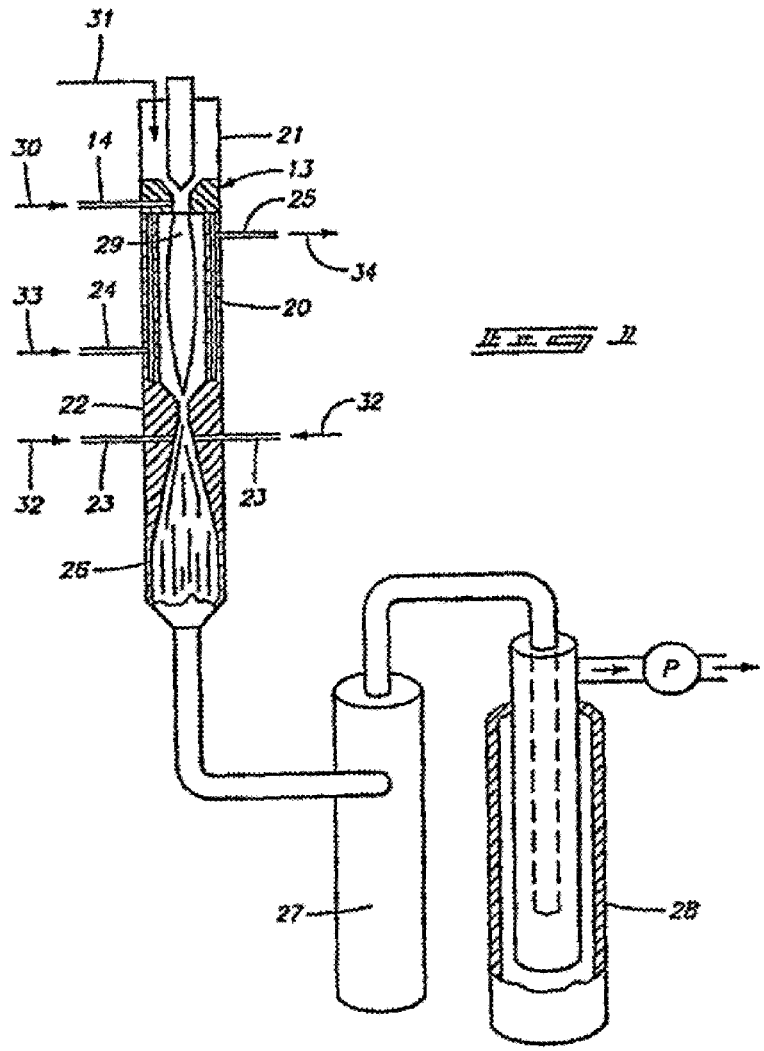

UNITED STATES PATENT AND TRADEMARK OFFICE
CERTIFICATE OF CORRECTION

PATENT NO.       : 5,935,293
APPLICATION NO.  : 09/076922
DATED            : August 10, 1999
INVENTOR(S)      : Brent A. Detering et al.

It is certified that error appears in the above-identified patent and that said Letters Patent is hereby corrected as shown below:

In the specification:

| | | |
|---|---|---|
| COLUMN 5, | LINE 60, | change "produces hydrogen" to --produces a hydrogen-- |
| COLUMN 6, | LINE 25, | change "FIG. 8 are side and top cross sectional views" to --FIG. 8 shows side and top cross-sectional views-- |
| COLUMN 6, | LINE 59, | change "to the left)" to --at its upper end)-- |
| COLUMN 6, | LINE 60, | change "to the right)." to --at its lower end).-- |
| COLUMN 6, | LINE 62, | change "chamber." to --chamber 20.-- |
| COLUMN 8, | LINE 14, | change "vacuum pump 29." to --vacuum pump P.-- |
| COLUMN 8, | LINE 21, | change "pump 29." to --vacuum pump P.-- |
| COLUMN 11, | LINE 12, | change "$P_0, P_1, T_0$ are" to -- $P_0, P_1, T_0$ and $T_1$ are-- |
| COLUMN 11, | LINE 36, | change "for constant $\gamma$" to --for a constant value of $\gamma$-- |
| COLUMN 13, | LINE 38, | change "fine (–20" to --fine (e.g., 20-- |
| COLUMN 21, | LINE 51, | change "cooper" to --copper-- |
| COLUMN 25, | LINE 67, | change "chamber 23 to" to --chamber 20 to-- |
| COLUMN 26, | LINE 1, | change "impedence 35." to --impedance 35.-- |

In the claims:

| | | | |
|---|---|---|---|
| CLAIM 15, | COLUMN 27, | LINE 50, | change "comprising the" to --comprising:-- |
| CLAIM 15, | COLUMN 27, | LINE 51, | delete "following step:" |
| CLAIM 15, | COLUMN 28, | LINE 1, | change "through a converging" to --through the converging-- |
| CLAIM 16, | COLUMN 28, | LINE 3, | change "comprising the" to --comprising:-- |
| CLAIM 16, | COLUMN 28, | LINE 4, | delete "following step:" |
| CLAIM 22, | COLUMN 28, | LINE 26, | change "wherein" to --further comprising introducing-- |
| CLAIM 22, | COLUMN 28, | LINE 27, | delete "is added" and change "after it" to --after the reactant stream-- |
| CLAIM 23, | COLUMN 28, | LINE 33, | change "comprising the following steps:" to --comprising:-- |
| CLAIM 23, | COLUMN 28, | LINE 36, | change "the reactor chamber having" to --defining the reactor chamber to exhibit-- |

UNITED STATES PATENT AND TRADEMARK OFFICE
CERTIFICATE OF CORRECTION

PATENT NO. : 5,935,293
APPLICATION NO. : 09/076922
DATED : August 10, 1999
INVENTOR(S) : Brent A. Detering et al.

It is certified that error appears in the above-identified patent and that said Letters Patent is hereby corrected as shown below:

In the claims (continued):
CLAIM 23, COLUMN 28, LINE 40, change "adjacent the outlet" to --adjacent an outlet--

Signed and Sealed this

Twentieth Day of February, 2007

JON W. DUDAS
*Director of the United States Patent and Trademark Office*